US006978170B1

(12) United States Patent
Onda et al.

(10) Patent No.: US 6,978,170 B1
(45) Date of Patent: Dec. 20, 2005

(54) BODY FAT MEASURING METHOD AND DEVICE THEREFOR

(75) Inventors: Tomohiro Onda, Tochigi (JP); Masaki Fukuhara, Tokyo (JP); Kazuo Maki, Tochigi (JP); Toru Yamaguchi, Tochigi (JP); Mitsuhiro Katashima, Tochigi (JP); Tsuyoshi Kimura, Tochigi (JP)

(73) Assignee: Kao Corporation, Tokyo (JP)

( * ) Notice: Subject to any disclaimer, the term of this patent is extended or adjusted under 35 U.S.C. 154(b) by 660 days.

(21) Appl. No.: 10/089,097

(22) PCT Filed: Oct. 5, 2000

(86) PCT No.: PCT/JP00/06949

§ 371 (c)(1),
(2), (4) Date: Aug. 1, 2002

(87) PCT Pub. No.: WO01/26546

PCT Pub. Date: Apr. 19, 2001

(30) Foreign Application Priority Data

| Oct. 15, 1999 | (JP) | ................................. 11-294431 |
| Jan. 7, 2000 | (JP) | ............................ 2000-001917 |
| Jan. 7, 2000 | (JP) | ............................ 2000-001921 |

(51) Int. Cl.$^7$ ............................................. A61B 5/05
(52) U.S. Cl. .................................................... 600/547
(58) Field of Search ................................ 600/547, 587

(56) References Cited

U.S. PATENT DOCUMENTS 5,335,667 A   8/1994   Cha et al.

FOREIGN PATENT DOCUMENTS

| GB | 2 160 323 | 12/1985 |
| JP | 11-113870 | 4/1999 |
| JP | 11-123182 | 5/1999 |
| JP | 11-309123 | 11/1999 |
| JP | 2000-175875 | 6/2000 |
| JP | 2000-225100 | 8/2000 |
| JP | 2000-350710 | 12/2000 |
| JP | 2000-350727 | 12/2000 |
| JP | 2001-104271 | 4/2001 |
| JP | 2001-212111 | 8/2001 |
| JP | 2001-286452 | 10/2001 |
| WO | 97/01303 | 1/1997 |

OTHER PUBLICATIONS

Katsuyuki Sakamoto: "An Impedance CT method" Japanese Society for Medical and Biological Engineering, vol. 8, No. 8, pp. 49-56 1994.

Primary Examiner—Eric F. Winakur
(74) Attorney, Agent, or Firm—Oblon, Spivak, McClelland, Maier & Neustadt, P.C.

(57) ABSTRACT

Two current electrodes 2 and 3 are arranged on a circumference of a subject 1, a distance between the two current electrodes being sufficiently shorter than a circumferential length of the subject 1. A current source 4 passes a current between the two current electrodes. A measuring electrode 5 is arranged adjacent to one of the two current electrodes 2 and 3. A measuring electrode 11 is arranged substantially opposite to the two current electrodes 2 and 3 across the subject 1. A voltmeter 7 measures a voltage generated between the measuring electrodes 5 and 11. A body fat computing unit 25 computes the quantity of subcutaneous fat 8 of the subject 1 according to the voltage measured with the voltmeter 7.

41 Claims, 18 Drawing Sheets

ELECTRODE POSITION

THICKNESS OF SUBCUTANEOUS FAT d

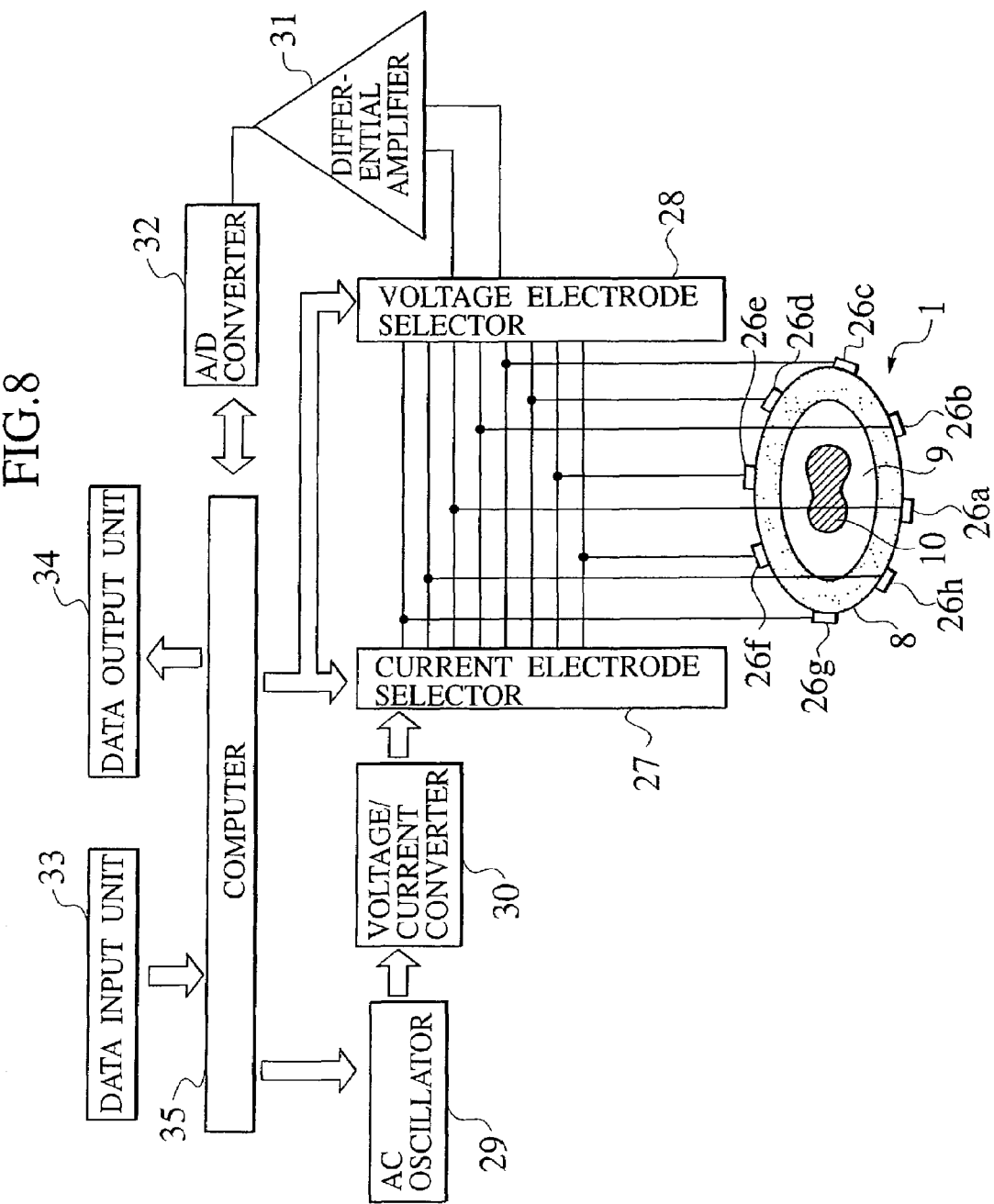

BODY FAT MEASURING METHOD AND DEVICE THEREFOR

TECHNICAL FIELD

The present invention relates to a method of and an apparatus for easily and accurately measuring layered subcutaneous fat and visceral fat in a human body.

BACKGROUND ART

An impedance CT system utilizes the fact that media have individual electric impedance values, to find spatial media distributions in a three-dimensional object. The impedance CT system passes a current through an object, measures a potential distribution induced at the surface of the object, and visualizes an impedance distribution in the object according to the potential distribution. The system is applicable to measuring the distributions of blood, lungs, fat, etc., in a human body ("BME" Vol. 8, No. 8 (1994), p. 49, Japanese Society for Medical and Biological Engineering).

In addition to the impedance CT system, there are other apparatuses that measure electric impedance values and find subcutaneous and visceral fat quantities. An example of such apparatuses is "Body Fat Measuring Apparatus" disclosed in Japanese Patent Laid Open Publication No. 11-113870 (first prior art). Another example is "Internal Fat Measuring Instrument" disclosed in Japanese Patent Laid Open Publication No. 11-123182 (second prior art). The first prior art attaches a plurality of electrodes to the surface of a body, measures impedance values between the electrodes, and creates an impedance matrix for a cross section of the body. Thereafter, an operation unit calculates the product of the impedance matrix and a coefficient matrix prepared from information on the electrode attached parts of the body entered through an input unit, and provides a cross-sectional body fat distribution. The second prior art winds a belt around the body of a subject. The inner side of the belt is provided with electrode pairs each consisting of a current path forming electrode and measuring electrode. The electrode pairs are arranged substantially at regular intervals. Two electrode pairs are chosen, and an AC current is passed between the current path forming electrodes of the chosen electrode pairs, to form a current path. The measuring electrodes measure an impedance value in the current path. The two electrode pairs are properly chosen so that adjacent electrodes may mainly measure subcutaneous fat and opposing electrodes may mainly measure visceral fat.

DISCLOSURE OF INVENTION

The impedance CT system involves an insufficient spatial resolution when estimating an internal fat distribution, and therefore, is insufficient to correctly calculate a body fat quantity. In addition, the system must carry out many numerical operations to find a body fat quantity.

The first prior art shows no concrete description how to form a coefficient matrix for electrode attached parts and how to create a cross sectional body fat distribution image from the product of impedance and coefficient matrixes.

The second prior art may measure a subcutaneous fat quantity at a measurement location on a human body. The measured fat quantity, however, includes the influence of the quantities and distributions of other media in the body, and therefore, is inaccurate. In addition, the second prior art is incapable of correctly measuring visceral fat of a human body due to the strong influence of layered subcutaneous fat in the body.

The present invention provides a body fat measuring method capable of easily and correctly measuring the quantity, such as thickness or cross-sectional area, of layered subcutaneous fat as well as the quantity of visceral fat in a human body. Also provided is an apparatus for achieving the method.

BEST MODE FOR CARRYING OUT THE INVENTION

A body fat measuring method according to the present invention includes a step of passing a current between two current electrodes arranged on a circumference of a subject, a distance between the electrodes being sufficiently shorter than a circumferential length of the subject, a step of measuring a first voltage generated between a first measuring electrode arranged adjacent to one of the two current electrodes and a second measuring electrode arranged substantially opposite to the two current electrodes across the subject, and a step of computing a subcutaneous fat quantity of the subject according to the first voltage.

The present invention includes a step of passing a current between two current electrodes arranged on a circumference of a subject substantially opposite to each other across the subject, a step of measuring a spatial potential gradient occurring on the circumference of the subject substantially at an intermediate position between the two current electrodes, and a step of computing a visceral fat quantity of the subject according to the spatial potential gradient.

The present invention also includes a step of passing a current between two current electrodes arranged on a circumference of a subject substantially opposite to each other across the subject, a step of measuring a voltage generated between two measuring electrodes that are each arranged adjacent to the two current electrodes, and a step of multiplying the voltage by a power of a characteristic quantity representing the size of the subject and computing the sum of subcutaneous and visceral fat quantities of the subject according to the product.

According to the present invention, "visceral fat quantity" collectively indicates the quantity of fat present inside a subject. That is, it indicates the quantity of visceral fat existing around internal organs of a subject and the quantity of general internal fat such as liver fat.

BRIEF DESCRIPTION OF DRAWINGS

FIG. 8 shows a body fat measuring apparatus according to a fourth embodiment based on the first aspect;

BEST MODE OF IMPLEMENTATION

Preferred embodiments of the present invention will be explained in detail with reference to the accompanying drawings.

First Aspect

A method of and an apparatus for measuring body fat according to the first aspect of the present invention measure the quantity, such as thickness or cross-sectional area, of layered subcutaneous fat in a human body.

Figure 1:
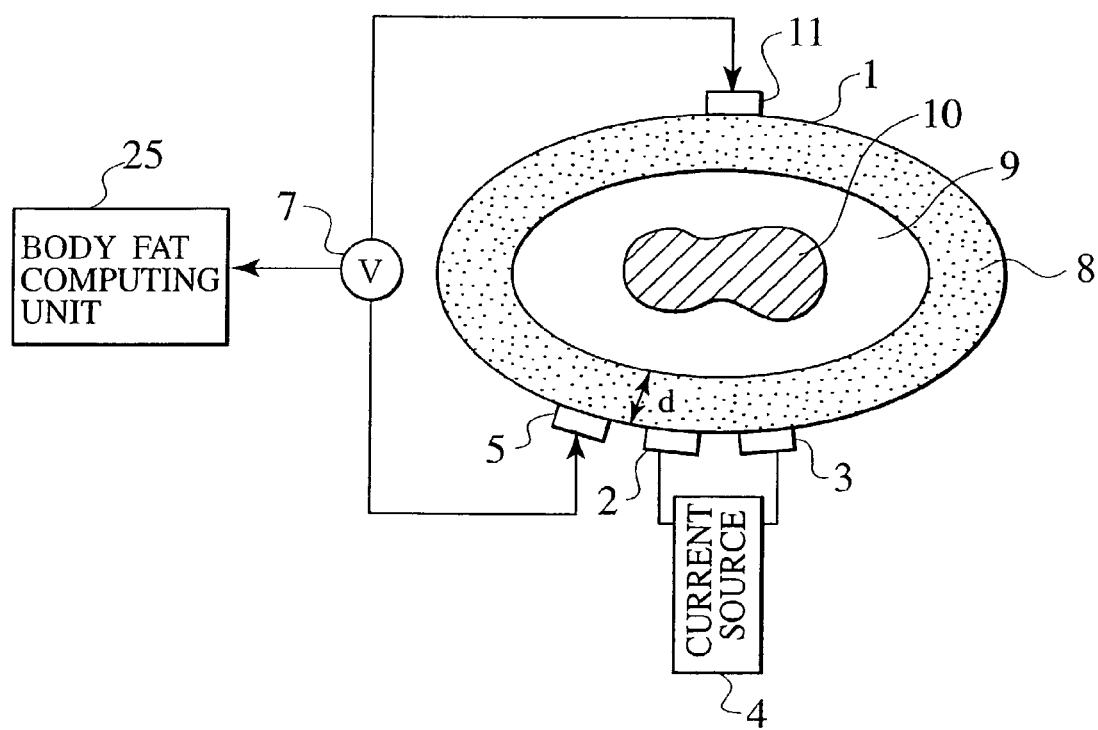
FIG. 1 shows a body fat measuring apparatus according to a first embodiment based on a first aspect.

FIG. 1 shows a body fat measuring apparatus according to a first embodiment based on the first aspect. The apparatus has two current electrodes 2 and 3 that are arranged on a circumference of, for example, the body of a subject (human) 1, a distance between the electrodes being sufficiently shorter than a circumferential length of the subject 1, a current source 4 to supply a current between the electrodes 2 and 3, a first measuring electrode 5 arranged adjacent to the electrode 2, a second measuring electrode 11 arranged substantially opposite to the electrodes 2 and 3 across the subject 1, a voltmeter 7 to measure a voltage generated between the electrodes 5 and 11, and a body fat computing unit 25 to compute the thickness of layered subcutaneous fat 8 of the subject 1 according to the voltage measured with the voltmeter 7. The subject 1 has the subcutaneous fat 8, a nonfat part 9, whose impedance differs from that of the subcutaneous fat 8, and visceral fat 10, whose impedance differs from that of the nonfat part 9. The body fat computing unit 25 may be a computer.

A body fat measuring method using the apparatus will be explained. The current source 4 passes a current between the electrodes 2 and 3 that are arranged on a circumferential surface of the subject 1. The distance between the electrodes 2 and 3 is sufficiently shorter than the circumferential length of the subject 1. The voltmeter 7 measures a voltage generated between the first and second measuring electrodes 5 and 11. The electrode 5 is arranged close to the electrode 2, and the electrode 11 is arranged opposite to the electrodes 2 and 3 across the subject 1. The computing unit 25 computes the thickness of the layered subcutaneous fat 8 of the subject 1 according to the measured voltage.

Figure 2:
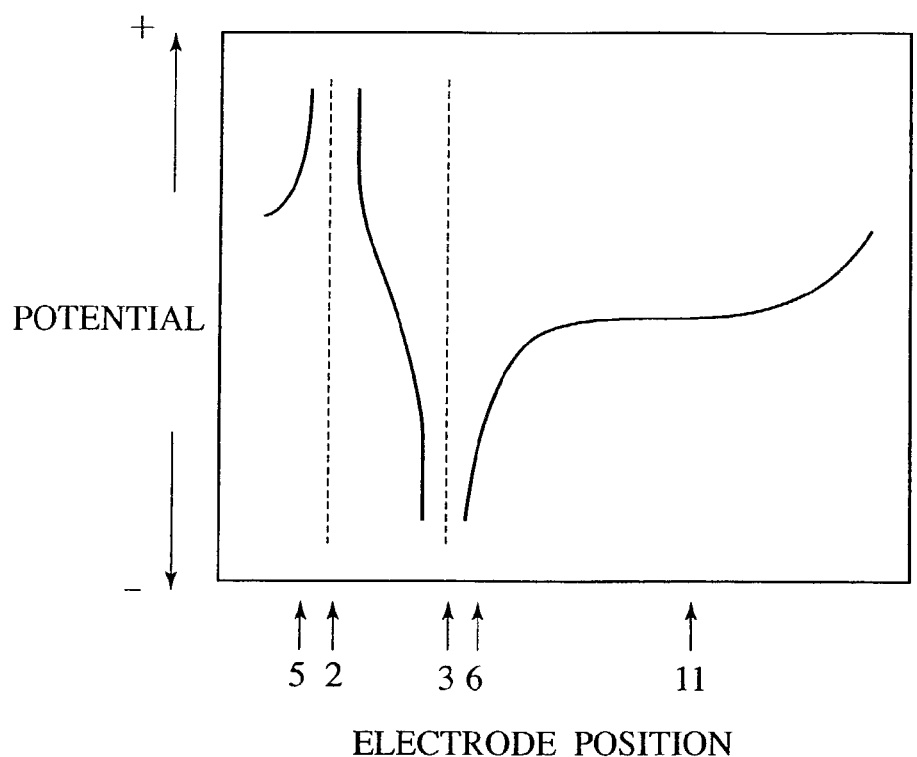
FIG. 2 shows a potential distribution on the circumference of a human body when a current is passed between current electrodes.

FIG. 2 roughly shows a distribution of potential (instantaneous values) induced on the circumference of the subject 1 in response to the current passed between the electrodes 2 and 3. Around the electrode 11, a spatial potential change is small, and therefore, the voltage V measured with the voltmeter 7 is stable even if the position of the electrode 11 is slightly shifted. The voltage V is substantially free from the quantities and distributions of the nonfat part 9 and visceral fat 10 in the subject 1, and therefore, it is possible to easily and precisely measure the thickness of the subcutaneous fat 8 around the electrodes 2, 3, and 5. Typically, the voltage V reflects the thickness d of the subcutaneous fat 8 substantially at an intermediate position between the current electrode 2 and the first measuring electrode 5.

The current source 4 may be of any one of DC and AC. If the current source 4 is an AC current source, a phase delay may simultaneously be measured when the voltmeter 7 measures a voltage (amplitude or effective value) and thereby the measured phase delay is usable to analyze data. When measuring a human body, AC is easier to handle and the frequency of the AC current source may be 10 kHz to 500 kHz, preferably 50 kHz to 200 kHz, and a current value may be 0.3 mA to 3 mA.

To compute the thickness d of the subcutaneous fat 8 around the electrodes 2, 3, and 5, it is necessary to prepare a correlation expression to correlate a voltage V (or complex voltage) with the thickness d of the subcutaneous fat 8. To prepare such a correlation expression, a plurality of samples consisting of the same media and having different thicknesses d must be examined. Based on the samples, a correlation expression is prepared to correlate a voltage V measured according to the method of FIG. 1 with an actual thickness d. When measuring voltages V on the samples, the same current or different currents are applied to the samples. When different currents are used, measured voltages must be normalized based on one current. To measure actual thicknesses d on the samples, an X-ray CT system or an MRI system may provide tomographic images of the samples, and based on the images, subcutaneous fat thicknesses of the samples can be estimated. If the samples are not human bodies, they may be mechanically sliced to directly measure their thicknesses. The samples may have known internal structures. The correlation expression to correlate a voltage V (or complex voltage) with the thickness d of the subcutaneous fat 8 may be found from numerical calculations by solving electric conduction equations by computer. The correlation expression is dependent on the surface curvature of the subject 1 and an interface structure between the subcutaneous fat 8 and the nonfat part 9, and therefore, differs depending on the part (navel area, flank, back, and the like) where the thickness of the subcutaneous fat 8 is measured. When measuring subcutaneous fat thicknesses at different locations on the subject 1, it is preferable to prepare a correlation expression for each of the locations.

The thickness d of the subcutaneous fat 8 may be expressed in an absolute value or a ratio (relative value) with respect to a length reflecting a cross-sectional length of the subject 1, such as a circumferential length U of the subject 1. From among them, an optimum one is chosen.

Figure 3:
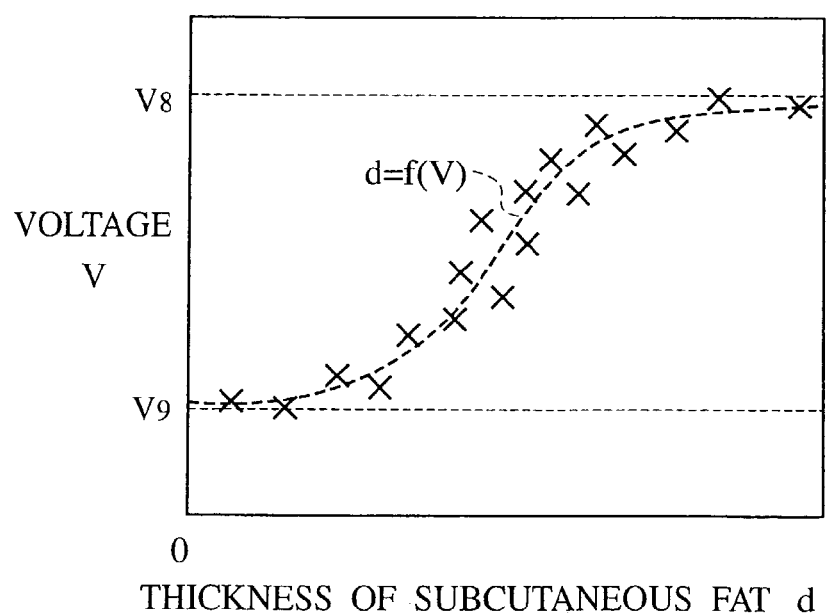
FIG. 3 shows a correlation between subcutaneous fat thickness and voltage.

FIG. 3 shows an example of a correlation between voltage V and the thicknesses d of the subcutaneous fat 8. In FIG. 3, crosses represent data points concerning samples prepared for making a correlation expression, and a dotted curve indicates the correlation expression formed by properly tracing the data points. As the thickness d of subcutaneous fat increases, the voltage V converges to a value V8 reflecting the impedance of the subcutaneous fat 8. As the thickness d decreases, the voltage V converges to a value V9 reflecting the impedance of the nonfat part 9. This correlation may be approximated by an analytic function, e.g., a hyperbolic tangent function (y=tanh x). The correlation expression to correlate a voltage V with a thickness d may be approximated by a multivariate analysis, e.g., a linear polynomial involving the voltage V. If the thickness d is an absolute thickness of the subcutaneous fat 8, it will be expressed as, for example, $d=a0+a1 \cdot V \cdot U+a2 \cdot U+a3/U$, where a0, a1, a2, and a3 are regression coefficients and U is a circumferential length of the subject 1. If the thickness d is a relative value corresponding to the thickness of the subcutaneous fat 8, the correlation expression is, for example, $d=a0+a1 \cdot V+a2/U+a3/U^2$. In FIG. 3, the impedance of the subcutaneous fat 8 is greater than that of the nonfat part 9, and the voltage V is an increasing function of the thickness d. Once the correlation expression is prepared, the subcutaneous fat thickness of a sample composed of the same media is calculable by passing a current between the electrodes 2 and 3 and solving the correlation expression according to a voltage measured with the voltmeter 7.

The distance between the current electrodes 2 and 3 is preferably less than 1/6, more preferably, 1/8 of the circumferential length of the subject 1. If the distance between the electrodes 2 and 3 is too large, a current supplied between them will flow deeply inside the subject 1. Then, a measured voltage V is affected by the distributions and quantities of the nonfat part 9 and visceral fat 10. If the distance between the electrodes 2 and 3 is too small, measuring sensitivity will deteriorate on samples having thick subcutaneous fat 8, and the measured voltage V will be affected by the shapes and sizes of the electrodes.

Figure 4:
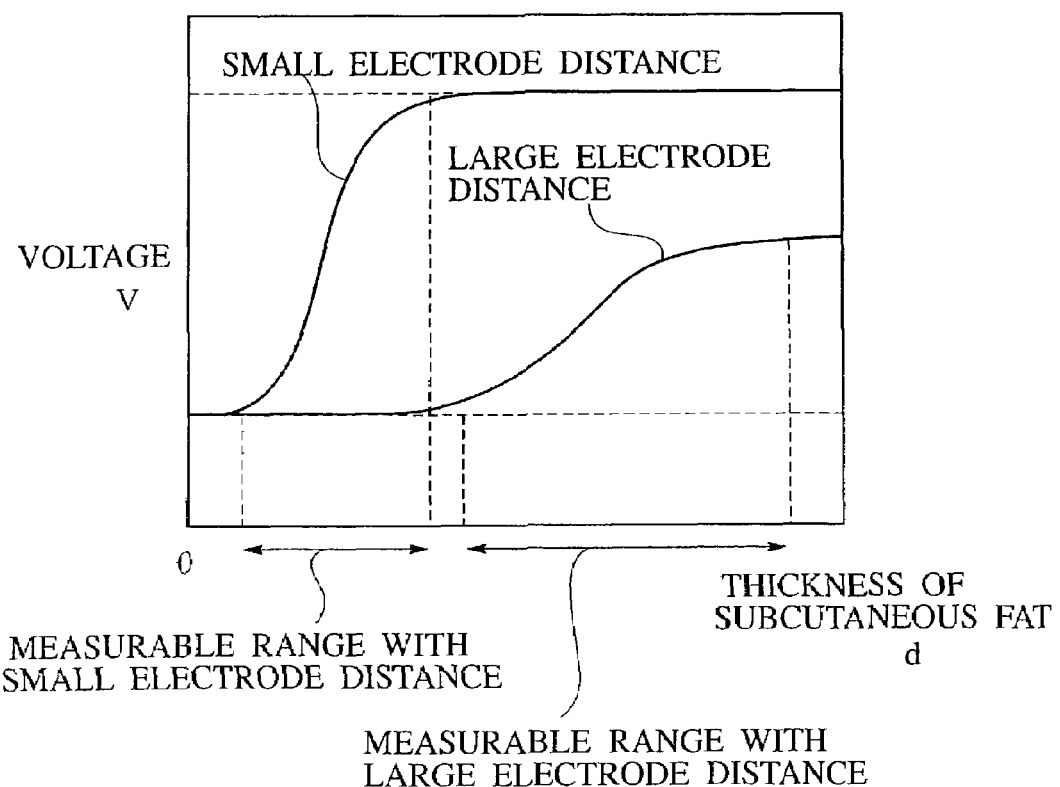
FIG. 4 shows relationships among electrode-to-electrode distance, subcutaneous fat thickness, and voltage.

The distance between the measuring electrode 5 and the current electrode 2 must be in a proper range. If the distance is too large, the distributions and quantities of the nonfat part 9 and visceral fat 10 will affect a measured voltage V. In addition, measuring sensitivity deteriorates on samples having thin subcutaneous fat, as shown in FIG. 4. If the distance is too small, measuring sensitivity deteriorates on samples having thick subcutaneous fat, as shown in FIG. 4. In addition, the shapes and sizes of the electrodes and contact states between the electrodes and the subject 1 affect a measured voltage V. The distance between the measuring electrode 5 and the current electrode 2 is preferably 0.5 to 3 times an average thickness of the subcutaneous fat of a sample. If the thickness of the subcutaneous fat 8 is 1 to 4 cm, the distance (center-to-center distance) between the current electrodes is preferably 1 cm to 15 cm, more preferably, 2 cm to 10 cm. The distance (center-to-center distance) between the current electrode 2 and the adjacent measuring electrode 5 is preferably 0.6 cm to 10 cm, more preferably, 1 cm to 6 cm. The shapes of the electrodes are, for example, disks or rectangles. If disk electrodes are employed, they may have a diameter of 0.6 cm to 3.5 cm, preferably, 1.5 cm to 2.5 cm.

When measuring samples for preparing the correlation expression or when measuring a sample having an unknown thickness d, it is convenient to vary the distance between the current electrodes and the distance between the current electrodes and the measuring electrode in proportion to the circumferential length of a sample, or fix the electrode-to-electrode distances to the optimum values mentioned above without regard to the circumferential lengths of samples. If the samples have a wide variety of thicknesses d ranging from thin to thick and if it is unable to measure the thicknesses with the fixed electrode-to-electrode distances, a plurality of measuring systems having individual electrode-to-electrode distances are prepared and properly used depending on the thickness of a sample.

Figure 5:
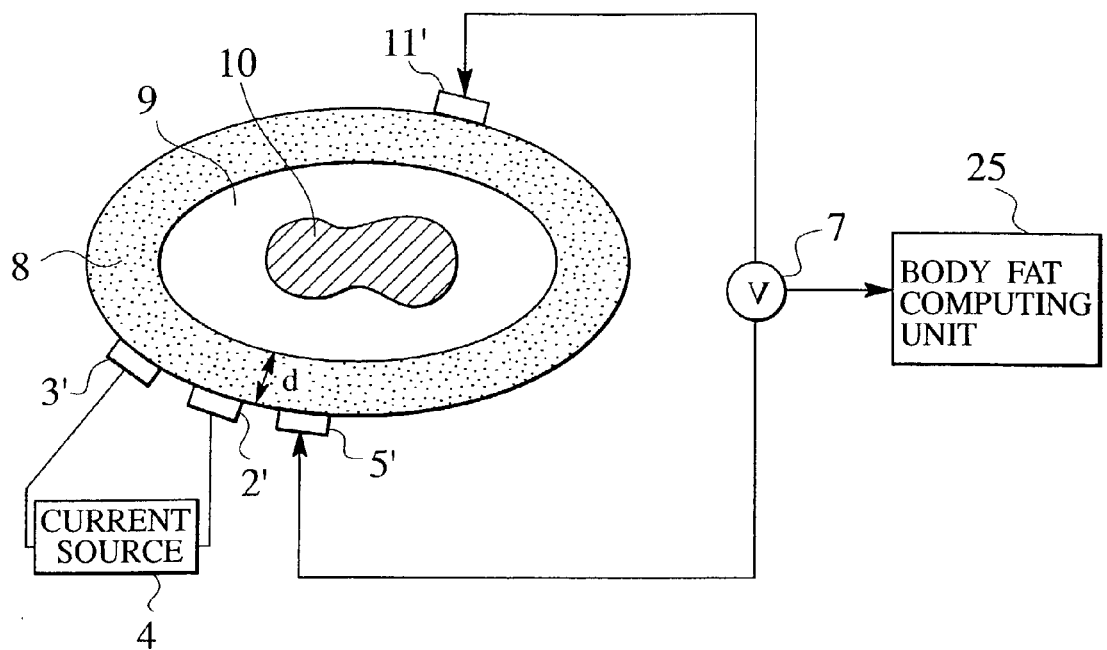
FIG. 5 shows another example of a body fat measuring apparatus according to the first embodiment based on the first aspect.

An apparatus of FIG. 5 may be added to the apparatus of FIG. 1, to improve computation accuracy of the thickness d of the subcutaneous fat 8. In FIG. 5, electrodes are arranged substantially symmetrically to those of FIG. 1 relative to a measuring point (an intermediate point between the electrodes 2 and 5) of the thickness d of the subcutaneous fat 8. Like the apparatus of FIG. 1, the apparatus of FIG. 5 employs a voltmeter 7 to measure a voltage V*, which also reflects the thickness d of the subcutaneous fat 8. An average of the voltage V* and the voltage V measured with the apparatus of FIG. 1 is calculated, and a correlation expression to correlate the average voltage with the thickness d of the subcutaneous fat 8 is prepared. Then, such an average voltage is usable to precisely calculate the thickness d of the subcutaneous fat 8.

The second embodiment will be explained. A body fat measuring apparatus according to the second embodiment based on the first aspect is formed by adding an apparatus of FIG. 6 to the apparatus of FIG. 1. The apparatus of FIG. 6 has two current electrodes 2 and 12 arranged substantially opposite to each other across the subject 1, a current source 4, measuring electrodes 13 and 14 arranged on the circumferential surface of the subject 1 substantially at an intermediate position between the electrodes 2 and 12, a voltmeter 15 to measure a voltage generated between the measuring electrodes 13 and 14, and a body fat computing unit 25 to correct the voltage measured with the voltmeter 7 of FIG. 1 according to the voltage measured with the voltmeter 15 and compute the thickness of the subcutaneous fat 8 according to the corrected voltage.

A body fat measuring method will be explained. In the apparatus of FIG. 1, the current source 4 passes a current between the electrodes 2 and 3, and the voltmeter 7 measures a first voltage generated between the first measuring electrode 5 arranged adjacent to the electrode 2 and the second measuring electrode 11 arranged substantially opposite to the current electrodes 2 and 3 across the subject 1.

Figure 6:
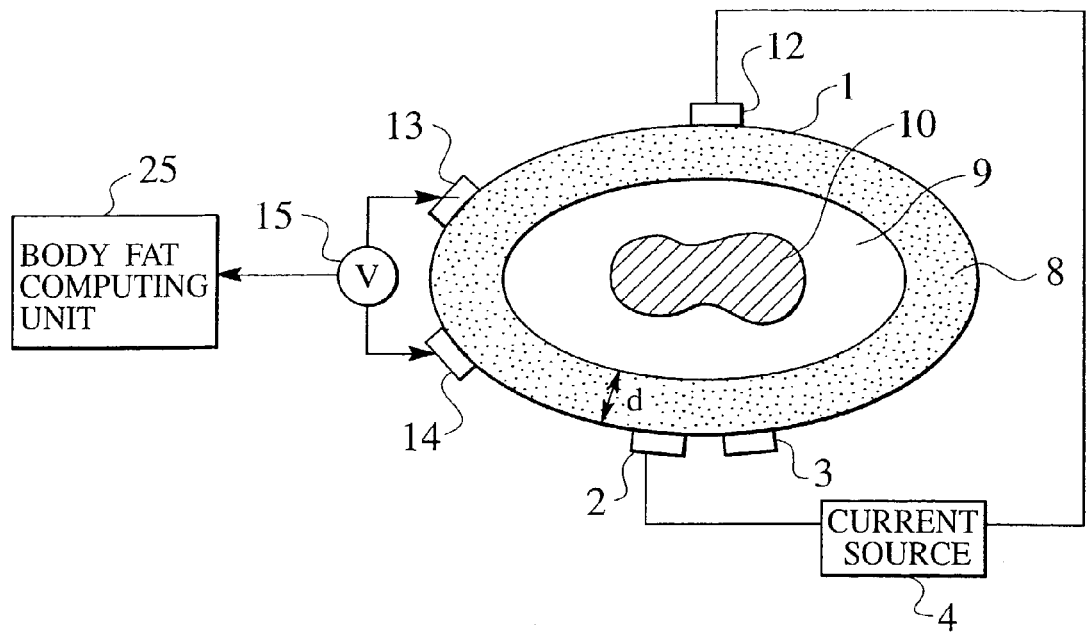
FIG. 6 shows a body fat measuring apparatus according to a second embodiment based on the first aspect.

In the apparatus of FIG. 6, the current source 4 passes a current between the electrodes 2 and 12. The voltmeter 15 measures a second voltage generated between the electrodes 13 and 14. The body fat computing unit 25 uses the second voltage measured with the voltmeter 15 to correct the first voltage measured with the voltmeter 7 and computes the thickness of the subcutaneous fat 8 according to the corrected voltage.

The first voltage V measured with the voltmeter 7 slightly involves the influence of the distributions and quantities of the nonfat part 9 and visceral fat 10 in the subject 1. This influence is removable by using the second voltage (impedance) V' measured in another current path made by the electrodes 2 and 12. This improves the measuring accuracy of the thickness of the subcutaneous fat 8.

The correction with the second voltage is made according to a correlation expression. A better correlation expression may be prepared by applying V+a'V' to the ordinate of FIG. 3 and by selecting an optimum value for the coefficient a'. Alternatively, the correlation expression may be approximated by a linear polynomial based on a multivariate analysis. If the thickness d of the subcutaneous fat 8 is an absolute value, regression coefficients a0, a1, a2, a3, and a4, the circumferential length U of the subject 1, and the distance L between the measuring electrodes 13 and 14 are used to express the thickness as, for example, $d=a0+a1 \cdot V \cdot U+a2 \cdot (V' \cdot U/L) \cdot U+a3 \cdot U+a4/U$. If the thickness d of the subcutaneous fat 8 is a relative value, the thickness is expressed as, for example, $d=a0+a1 \cdot V+a2 \cdot V' \cdot U/L+a3/U+a4/U^2$. Such a correlation expression is useful to precisely measure the thickness d of subcutaneous fat of a sample on the basis of voltages V and V' measured on the sample.

The apparatus of FIG. 5 may be added to the apparatuses of FIGS. 1 and 6, to further improve the measuring accuracy of the thickness d of the subcutaneous fat 8. That is, the voltage V measured with the apparatus of FIG. 1 and the voltage V* measured with the apparatus of FIG. 5 are averaged, and the average is corrected according to the voltage V' measured with the apparatus of FIG. 6, to compute the thickness d of the subcutaneous fat 8. In this case, the ordinate of FIG. 3 is $(V+V^*)/2+a' \cdot V'$ and an optimum value is selected for the coefficient a'. Alternatively, V is replaced with $(V+V^*)/2$ in the above-mentioned correlation expression.

The third embodiment will be explained. A body fat measuring apparatus according to the third embodiment consists of a measuring apparatus of FIG. 7A and a measuring apparatus of FIG. 7B. The apparatus of FIG. 7A has two current electrodes 2 and 3 that are arranged on a subject 1, a distance between the electrodes being sufficiently shorter than a circumferential length of the subject 1, a current source 4, measuring electrodes 5 and 6 arranged adjacent to the electrodes 2 and 3, a voltmeter 7 to measure a voltage generated between the electrodes 5 and 6, and a body fat computing unit 25 to receive the measured voltage. The measuring apparatus of FIG. 7B is the same as that of FIG. 6, and therefore, an explanation thereof is omitted. The conditions of the first embodiment including the technique of preparing a correlation expression to correlate a voltage with a thickness, the distance between the current electrodes, and the distances between the current electrodes and the measuring electrodes are applied to the third embodiment.

A body fat measuring method will be explained. In the measuring apparatus of FIG. 7A, the current source 4 passes a current between the electrodes 2 and 3. The voltmeter 7 measures a first voltage generated between the measuring electrodes 5 and 6.

In the measuring apparatus of FIG. 7B, the current source 4 passes a current between the current electrodes 2 and 12. The voltmeter 15 measures a second voltage generated between the measuring electrodes 13 and 14. The body fat computing unit 25 uses the second voltage measured with the voltmeter 15 to correct the first voltage measured with the voltmeter 7, and according to the corrected voltage, computes the thickness of subcutaneous fat 8 around the electrodes 2, 3, 5, and 6. The correction of the first voltage based on the second voltage is carried out like the second embodiment. A correlation expression like that of the second embodiment is prepared to find a subcutaneous fat quantity according to the corrected voltage.

The fourth embodiment will be explained. FIG. 8 shows a body fat measuring apparatus according to the fourth embodiment. This apparatus sequentially passes currents in a plurality of directions and automatically measures the thickness of subcutaneous fat 8 of a subject 1 at a plurality of points along a circumference of the subject 1. In FIG. 8, a plurality of electrodes 26a to 26h are arranged on a circumference of the subject 1. The electrodes 26a to 26h are connected to a current electrode selector 27 and a voltage electrode selector 28.

A data input unit 33 enters electrode select data, which is transferred to the current electrode selector 27 according to an instruction from a computer 35. The current electrode selector 27 selects two of the electrodes 26a to 26h as current electrodes in operation. The output of an AC oscillator 29 is converted by a current/voltage converter 30, to supply a predetermined current between the current electrodes.

According to an instruction from the computer 35, the voltage electrode selector 28 selects measuring electrodes from among the remaining electrodes. A voltage generated between the measuring electrodes is fetched by the computer 35 through a differential amplifier 31 and an A/D converter 32. The above operations are repeated by sequentially selecting current electrodes and measuring electrodes according to instructions from the computer 35. The voltage data fetched by the computer 35 is converted into a voltage to be generated when a reference current is supplied. The converted voltage is applied to a correlation expression that is entered through the data input unit 33 and expresses a correlation between a voltage and a subcutaneous fat thickness d. The thickness d of the subcutaneous fat 8 is computed on the basis of the correlation expression, and is transferred from the computer 35 to a data output unit 34, which displays the thickness.

Figure 9:
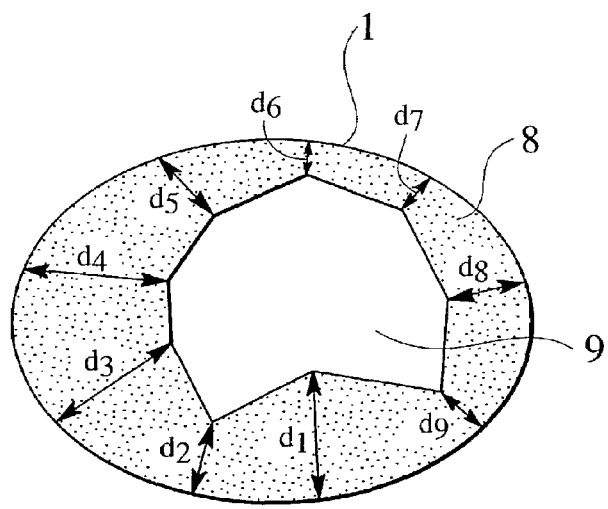
FIG. 9 shows computation of a tomographic image of subcutaneous fat in a human body.

Current electrodes are sequentially selected from among the electrodes 26a to 26h to provide, for example, the arrangement of current electrodes and measuring electrodes of FIG. 1 to precisely measure the thicknesses of the subcutaneous fat 8 at a plurality of locations along a circumference of the subject 1. The thicknesses of the subcutaneous fat 8 measured at a plurality of points along a circumference of the subject 1 may be combined with circumferential profile data of the subject 1 separately measured, to provide a rough tomographic image of the subcutaneous fat 8. FIG. 9 shows an example of a tomographic image of the subcutaneous fat 8 made from thicknesses d1 to d9 measured at nine points along a circumference of the subject 1.

The computer 35 may provide a cross-sectional area S of the subcutaneous fat 8 on a given section of the subject 1. To achieve this, a correlation expression to correlate voltages V with a cross-sectional area S is prepared. Measuring a voltage at a single point, e.g. at a flank, on the subject 1 may enable the cross-sectional area S to be roughly calculated. It is preferable to measure voltages V1 to Vn at n points along the circumference of a given section of the subject 1 and prepare a correlation expression to correlate the measured voltages with a cross-sectional area S of the subcutaneous fat 8. A circumferential length U along the cross section of the subject 1 may separately be measured and included in the correlation expression to improve the accuracy of the expression.

The correlation expression to correlate voltages (V1 to Vn) with a cross-sectional area S may be prepared like that to correlate a voltage V with a subcutaneous fat thickness d. The cross-sectional area S of subcutaneous fat 8 of a sample may be obtained by an X-ray CT system or an MRI system. If the sample is not a human body, it may be mechanically sliced to directly measure the cross-sectional area of the subcutaneous fat. The correlation expression may be approximated by a multivariate analysis, e.g., a linear polynomial. If the quantity S is the ratio (relative value) of the cross-sectional area of the subcutaneous fat 8 to the total cross-sectional area of the subject 1, the correlation expression is, for example, $S = a0 + a1 \cdot V1 + a2 \cdot V2 + \ldots + an \cdot Vn$, where $a0, a1, a2, \ldots$, and $an$ are regression coefficients. If the circumferential length U is included, the correlation expression is, for example, $S = a0 + a1 \cdot V1 + a2 \cdot V2 + \ldots + an \cdot Vn + b1/U + b2/U^2$, where b1 and b2 are regression coefficients. If the quantity S is an absolute cross-sectional area of the subcutaneous fat 8, the correlation expression is, for example, $S = a0 + (a1 \cdot V1 + a2 V2 + \ldots + an \cdot Vn) \cdot U^2 + b1 \cdot U + b2 \cdot U^2$. These correlation expressions make it possible to compute the cross-sectional area S of subcutaneous fat of a sample according to a set of voltages (V1 to Vn), or a set of voltages and a circumferential length (V1 to Vn and U) measured on the sample.

It is possible to find a volume B of the subcutaneous fat 8. In this case, voltages V1 to Vn (n being a natural number) are measured at a plurality of points on the subject 1, and a correlation expression is prepared to correlate the measured voltages with the volume B of the subcutaneous fat 8. The circumferential length and/or weight B0 and/or a weight-height ratio of the subject 1 are separately measured, and they may be included in the correlation expression to improve the accuracy of the expression. The volume of the subcutaneous fat 8 is, for example, that of the body, thigh, or upper arm of the subject 1. In any case, the electrodes are arranged along a circumference of the part to measure.

The correlation expression to correlate a set of voltages (V1 to Vn) with a volume B may be prepared like that to correlate a voltage V with a subcutaneous fat thickness. The volume B of the subcutaneous fat 8 in the subject 1 may be obtained by an X-ray CT system or an MRI system. If the quantity B is the ratio (relative value) of the volume of the subcutaneous fat 8 to the total volume of the measured part of the subject 1, the correlation expression is, for example, $B = a0 + a1 \cdot V1 + a2 \cdot V2 + \ldots + an \cdot Vn$, where a0 to an are regression coefficients. If the circumferential length U of the subject 1 is included, the correlation expression is, for example, $B = a0 + a1 \cdot V1 + a2 \cdot V2 + \ldots + an \cdot Vn + b1/U + b2/U^2$. If the weight B0 of the subject 1 is included, the correlation expression is, for example, $B = a0 + a1 \cdot V1 + a2 \cdot V2 + \ldots + an \cdot Vn + b1/B0^{1/2} + b2/B0$, where b1 and b2 are regressive coefficients. If the quantity B is an absolute volume of the subcutaneous fat 8, the correlation expression is, for example, $B = a0 + (a1 \cdot V1 + a2 \cdot V2 + \ldots + an \cdot Vn) \cdot U^2 + b1 \cdot U + b2 \cdot U^2$, or $B\ a0 + (a1 \cdot V1 + a2 \cdot V2 + \ldots + an \cdot Vn) \cdot U^2 + b1 \cdot B0^{1/2} + b2 \cdot B0$. These correlation expressions make it possible to compute the volume B of subcutaneous fat of a sample according to a set of voltages (V1 to Vn), or a set of voltages and a circumferential length (V1 to Vn and U), or a set of voltages and a weight (V1 to Vn and B0) measured on the sample. It is also possible to compute the weight, instead of volume, of the subcutaneous fat.

The electrodes 26a to 26h may be selected to constitute the arrangements of current electrodes and measuring electrodes of FIGS. 1 and 6. That is, two current electrodes 26a and 26b and two measuring electrodes 26h and 26e are selected, and thereafter, two current electrodes 26a and 26d and two measuring electrodes 26g and 26f are selected, to precisely measure the thickness of the subcutaneous fat 8 between the electrodes 26a and 26h. The current electrodes are sequentially selected to repeat measurements, to precisely provide the thicknesses of the subcutaneous fat 8 at a plurality of points along the circumference of the subject 1. The electrodes 26a to 26h may be selected to successively constitute the arrangements of current and measuring electrodes of FIGS. 1 and 5 and those of FIGS. 1, 5, and 6.

Figure 7A:
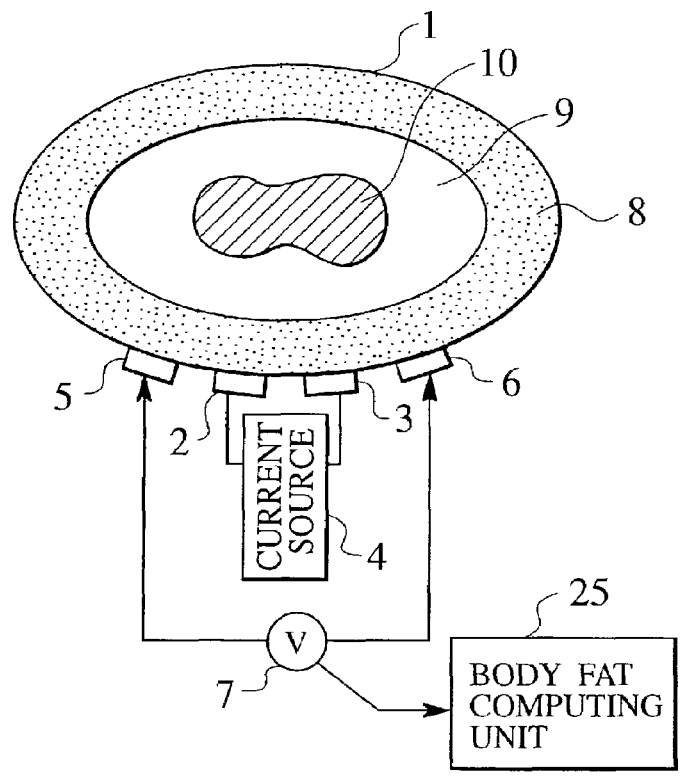
FIGS. 7A and 7B show a body fat measuring apparatus according to a third embodiment based on the first aspect.
Figure 7B:
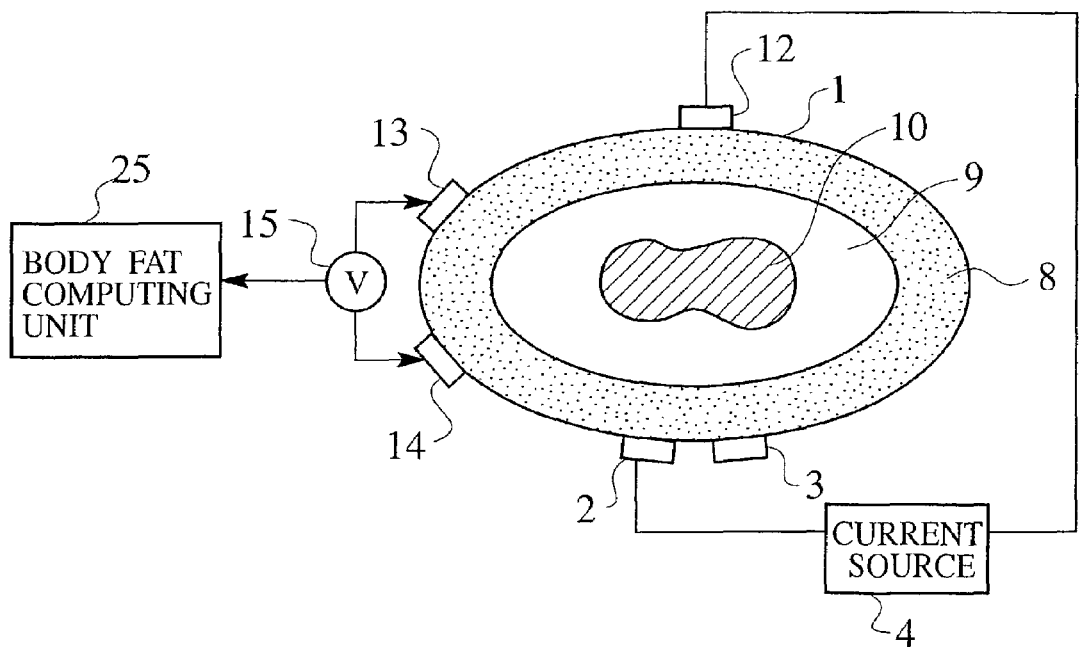

The electrodes 26a to 26h may be selected to constitute the arrangements of current and measuring electrodes of FIGS. 7A and 7B. That is, two current electrodes 26a and 26b and two measuring electrodes 26h and 26c are selected, and thereafter, two current electrodes 26a and 26d and two measuring electrodes 26g and 26f are selected, to precisely measure the thickness of the subcutaneous fat 8 around the electrodes 26a and 26b. The current electrodes are sequentially selected to repeat measurements, to precisely measure the thicknesses of the subcutaneous fat 8 at a plurality of points along a circumference of the subject 1. Correcting measured voltages eliminates the influence of the quantities and distributions of the nonfat part 9 and visceral fat 10 of the subject 1, to precisely measure the thickness, sectional area, or volume of the subcutaneous fat 8 of the subject 1.

According to the first to fourth embodiments, measurements may be carried out at a plurality of current frequencies, and the measurements may be compared with one another to improve the reliability of the measurements.

Second Aspect

A method of and an apparatus for measuring body fat according to the second aspect of the present invention measure a visceral fat quantity in a human body.

Figure 10:
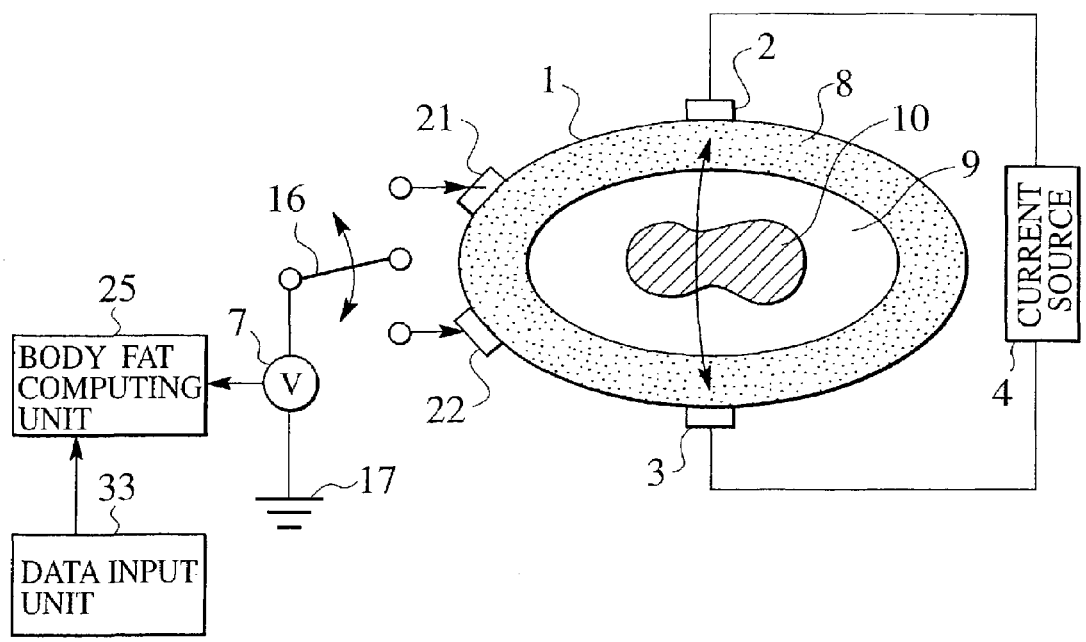
FIG. 10 shows a body fat measuring apparatus according to a first embodiment based on a second aspect.
Figure 11:
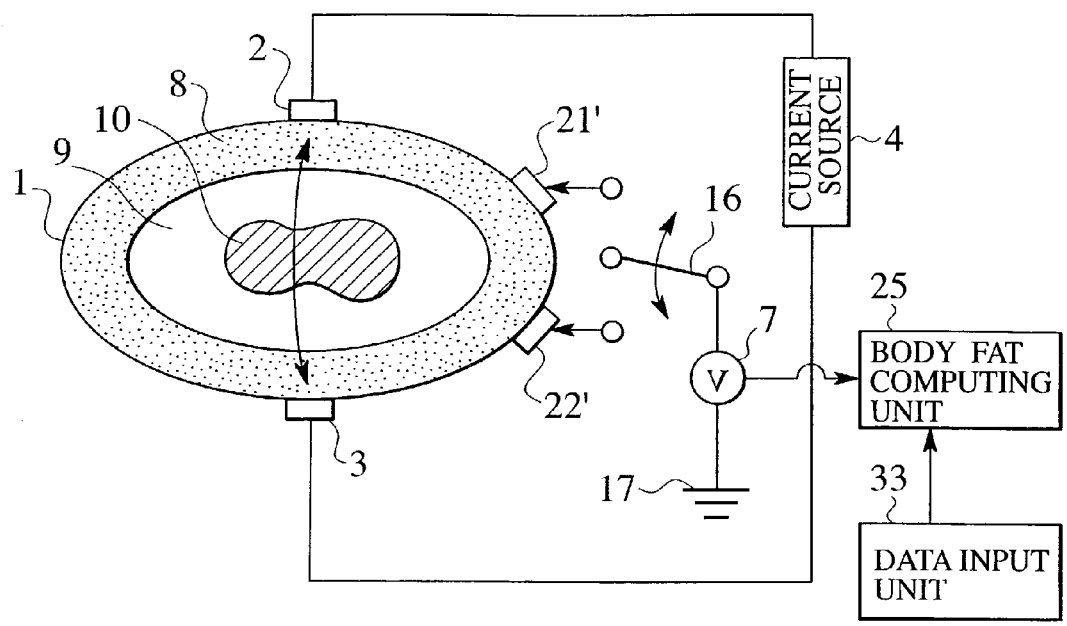
FIG. 11 shows another example of a body fat measuring apparatus according to the first embodiment based on the second aspect.

FIG. 10 shows a body fat measuring apparatus according to a first embodiment. The apparatus has two current electrodes 2 and 3 arranged on a circumference of a subject 1 substantially opposite to each other across the subject 1, a current source 4, two measuring electrodes 21 and 22 arranged on the circumference of the subject 1 substantially at an intermediate position between the current electrodes 2 and 3, a distance between the electrodes 21 and 22 being sufficiently smaller than a circumferential length of the subject 1, a reference potential 17 to measure the potential of the measuring electrodes 21 and 22, a switch 16 to connect the reference potential to the measuring electrode 21 or 22, a voltmeter 7 to measure the potential of the measuring electrodes 21 and 22, and a body fat computing unit 25 to compute the quantity of visceral fat 10 in the subject 1 according to the voltage measured with the voltmeter 7. The voltage may be measured at the other intermediate position between the current electrodes 2 and 3, as shown in FIG. 11, wherein measuring electrodes 21' and 22' are symmetrically arranged with respect to the measuring electrodes 21 and 22 of FIG. 10. The current electrodes 2 and 3 may be arranged on the back and abdomen of the subject 1, respectively, or on the flanks of the subject 1, respectively. To accurately measure a visceral fat quantity, it is preferable that the electrodes 2 and 3 are arranged on the back and abdomen of the subject 1, respectively. The number of current electrodes arranged on a circumference of the subject 1 may be more than 2 as shown in FIG. 12, if currents are passed across the subject 1.

The body fat measuring apparatuses of FIGS. 10 and 11 may have a data input unit 33 to enter data related to a circumferential length of the subject 1, the distance between the electrodes 21 and 22, and the distance between the electrodes 21' and 22'. The body fat computing unit 25 computes a visceral fat quantity according to the circumferential length of the subject 1, the distance between the electrodes 21 and 22, and the distance between the electrodes 21' and 22' entered through the data input unit 33 and a voltage measured with the voltmeter 7.

A body fat measuring method will be explained. The current source 4 passes a current between the current electrodes 2 and 3 that are arranged on a circumference of the subject 1 substantially opposite to each other across the subject 1. The switch 16 is switched so that the voltmeter 7 measures a voltage V1 between the measuring electrode 21 and the reference potential 17 and a voltage V2 between the measuring electrode 22 and the reference potential 17. The computing unit 25 computes a quantity m of the visceral fat 10 according to the voltages V1 and V2 measured with the voltmeter 7.

Figure 12:
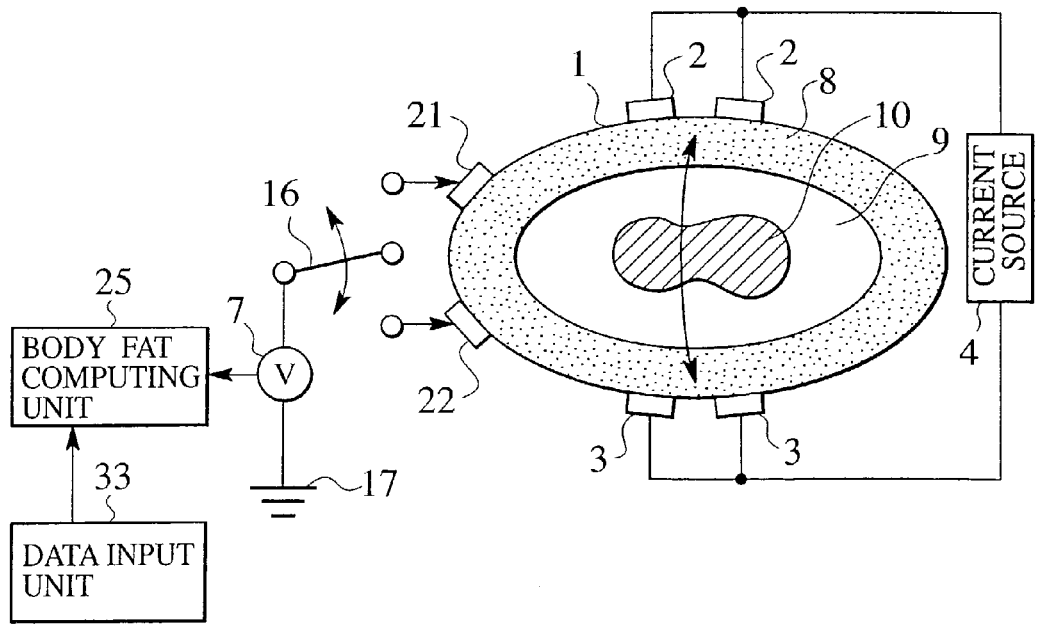
FIG. 12 shows another example of a body fat measuring apparatus according to the first embodiment based on the second aspect.

In FIGS. 10 to 12, the current source 4 may be of any one of DC and AC. If the current source 4 is an AC current source, a phase delay may simultaneously be measured when the voltmeter 7 measures a voltage (amplitude or effective value). The measured phase delay is used to analyze data. When measuring a human body, AC is easier to handle. The frequency of the AC current source may be 10 kHz to 500 kHz, preferably 50 kHz to 200 kHz, and a current value may be 0.3 mA to 3 mA.

Figure 13:
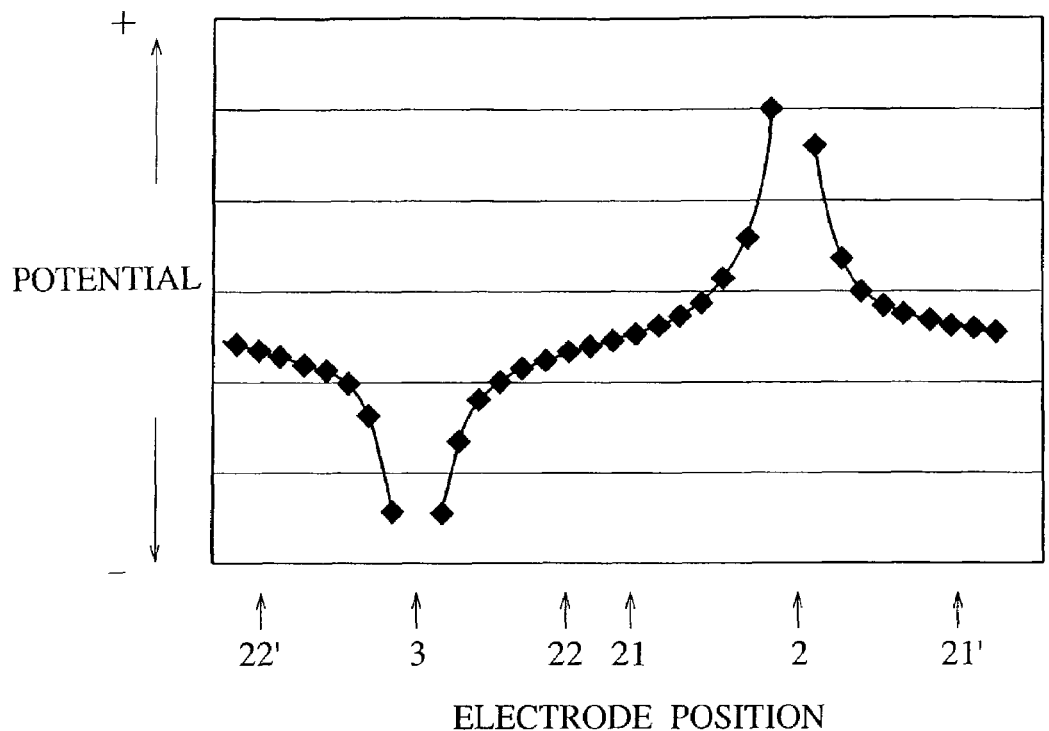
FIG. 13 shows a potential distribution on the circumference of a human body when a current is passed between current electrodes.

FIG. 13 shows a schematic distribution of potential (instantaneous values) induced on a circumference of the subject 1 in response to a current flowing from the electrode 2 to the electrode 3. The absolute value of a spatial potential gradient (inclination) around the electrodes 21 and 22, or 21' and 22', which is relatively small, strongly correlates to the quantity of the visceral fat 10. If the absolute value of the spatial potential gradient is large, the quantity of the visceral fat 10 is large, and if it is small, the quantity of the visceral fat 10 is small. The spatial potential gradient is substantially free from the quantity and distribution of subcutaneous fat 8 of the subject 1, and therefore, it is possible to easily and precisely measure the quantity m of the visceral fat 10 irrespective of the distribution and quantity of the subcutaneous fat 8.

The quantity m of the visceral fat 10 may be computed according to one of a spatial potential gradient around the electrodes 21 and 22 and that around the electrodes 21' and 22' or according to an average of the two spatial potential gradients. A person having a large visceral fat quantity generally has also a large total fat quantity (the sum of visceral and subcutaneous fat quantities), and therefore, the spatial potential gradient is usable to approximate the total fat quantity of the subject 1.

The spatial potential gradient may be a potential difference |V1−V2| where V1 is the voltage measured between the measuring electrode 21 and the reference potential 17 and V2 is the voltage measured between the measuring electrode 22 and the reference potential 17. |V1−V2| may be divided by a distance L12 between the electrodes 21 and 22, to use |V1−V2|/L12 as the spatial potential gradient. It is possible to use a more general spatial potential gradient $\zeta$ that is provided by normalizing the electrode distance as "L12/U" and dividing |V1−V2| by "L12/U" as $\zeta=|V1-V2|\cdot U/L12$.

To compute the quantity of the visceral fat 10, it is necessary to prepare a correlation expression to correlate a spatial potential gradient with the quantity of the visceral fat 10. To prepare the correlation expression, a plurality of samples having different fat quantities m are tested, and a correlation between spatial potential gradients measured with the method of any one of FIGS. 10 and 11 and actual visceral fat quantities m is found. When measuring voltages V1 and V2, the same current or different currents are applied to the samples. When different currents are used, measured voltages must be normalized based on one current. To measure actual visceral fat quantities m on the samples, an X-ray CT system or an MRI system may provide tomographic images of the samples to calculate the sectional areas and volumes of the visceral fat. If the samples are not human bodies, they may be mechanically sliced to directly measure sectional areas and volumes thereof. The samples may be those having known internal structures. When calculating a cross-sectional area from a tomographic image, current spreading may be considered. That is, not only the tomographic image of a target section but also the tomographic images of the vicinities of the target section may be prepared, and the sectional area of visceral fat of the target section is calculated from an average of the tomographic images. When computing a total fat quantity (the sum of visceral and subcutaneous fat quantities) from a spatial potential gradient, a correlation expression is prepared in the same manner.

The visceral fat quantity m may be expressed in the cross-sectional area or volume of the visceral fat 10, the ratio of the cross-sectional area of the visceral fat 10 to the total cross-sectional area of the subject 1, or the ratio of the cross-sectional area of the visceral fat 10 to the cross-sectional area of the nonfat part 9 around the visceral fat 10. Among them, a proper one showing an optimum correlation with a spatial potential gradient may be chosen in practice.

Figure 14:
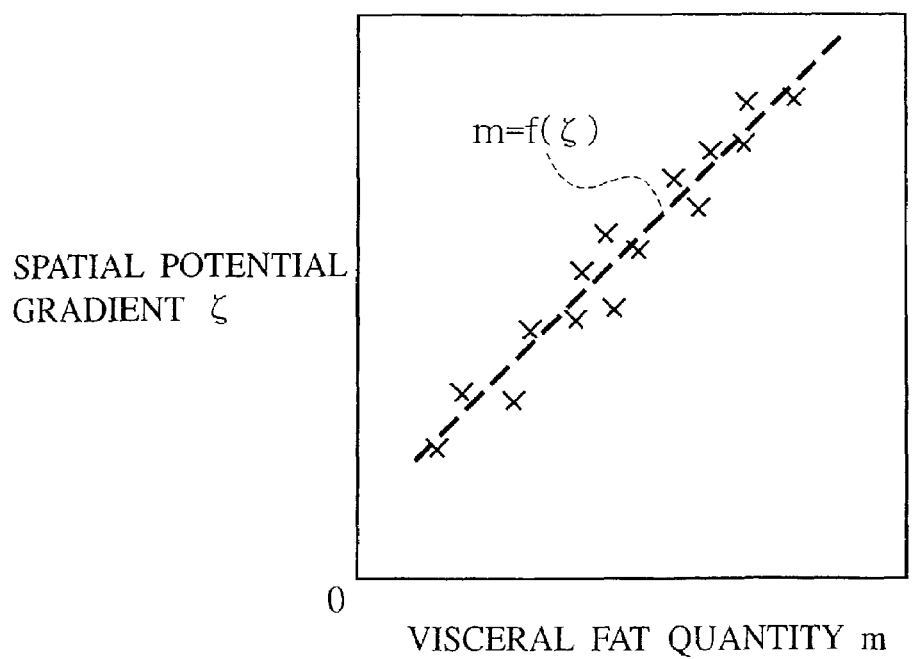
FIG. 14 shows a correlation between visceral fat quantity and spatial potential gradient.

The normalized spatial potential gradient $\zeta=|V1-V2|\cdot U/L12$ shows, in principle, a good correlation with the ratio of the cross-sectional area of the visceral fat 10 to the total cross-sectional area of the subject 1, or the ratio of the same to the cross-sectional area of the nonfat part 9 around the visceral fat 10. This is because a scaling law with respect to the potential distribution is almost satisfied, that is, the potential distribution of FIG. 13 is unchanged even if the subject 1 is similarly enlarged, as long as a current is kept constant. If a circumference of the subject 1 has a potential distribution V=g(x), a circumference of a subject 1' that is similarly larger or smaller than the subject 1 by $\zeta$ has a distribution roughly expressed as V=g(x'), where x'=$\zeta$x. To calculate a visceral fat quantity m from the spatial potential gradient $\zeta$, it is preferable to set the quantity m as the relative value mentioned above. FIG. 14 shows an example of a correlation between spatial potential gradient $\zeta$ and visceral fat quantity m. In FIG. 14, crosses indicate data points of samples for making a correlation expression, and a dotted line indicates a correlation expression formed by properly tracing the crosses. In FIG. 14, the impedance of visceral fat is greater than that of nonfat part, and $\zeta$ is an increasing function of visceral fat quantity m. The correlation expression m=f($\zeta$) to correlate a visceral fat quantity m with a spatial potential gradient $\zeta$ can be approximated by a linear function based on a multivariate analysis. In this case, the correlation expression will be m=a0+a1·$\zeta$, where a0 and a1 are regression coefficients. According to the correlation expression, the visceral fat quantity m of a sample is calculable from a spatial potential gradient $\zeta$ that is found from a voltage measured on the sample with the voltmeter 7.

On a sample having a constant circumferential length U, the normalized spatial potential gradient $\zeta$ becomes equivalent to the voltage |V1−V2| when the distance L12 between the electrodes 21 and 22 (or 21' and 22') is fixed. In this case, |V1−V2| is usable instead of $\zeta$. On a sample having a variable circumferential length U, the normalized spatial potential gradient $\zeta$ becomes equivalent to the voltage |V1−V2|, when the distance L12 between the electrodes 21 and 22 (or 21' and 22') is varied in proportion to the circumferential length U. In this case, |V1−V2| is also usable instead of $\zeta$. Changing the distance L12 between the electrodes 21 and 22 (or 21' and 22') is achievable by fixing the electrodes on a belt made of elastic material such as rubber and by winding the belt around the sample so that the belt may expand and contract on the sample. Another technique is to measure a circumferential length of the sample, and according to the length, mechanically change the electrode-to-electrode distance on the sample.

In FIG. 10 (or FIG. 11), it is preferable to properly set the distance between the electrodes 21 and 22 (or 21' and 22'). If the distance between the electrodes 21 and 22 is too small, a potential difference generated between the electrodes 21 and 22 is insufficient relative to measuring sensitivity. The distance between the electrodes 21 and 22 is preferably 3 cm or larger. If the distance between the electrodes 21 and 22 is too large, a measured voltage is affected by the distribution and quantity of the subcutaneous fat 8. Accordingly, the electrode-to-electrode distance is preferable to be ⅙ of the circumferential length or shorter. The shapes of the electrodes are, for example, disks or rectangles. If disk electrodes are employed, they may have a diameter of 0.6 cm to 3.5 cm, preferably, 1.5 cm to 2.5 cm.

An absolute visceral fat quantity of the subject 1 is calculable by multiplying the normalized spatial potential gradient $\zeta$ by a power of a characteristic quantity representing the size of the subject 1. This technique generally realizes a higher accuracy than calculating a relative value of visceral fat from the normalized spatial potential gradient $\zeta$. The absolute visceral fat quantity is preferably a cross-sectional area of the visceral fat 10 on or close to the cross section around which the electrodes are arranged. It is possible to approximate the absolute total fat quantity by multiplying the normalized spatial potential gradient $\zeta$ by a power of the characteristic quantity representing the size of the subject 1. In this case, the absolute total fat quantity is preferably the total cross-sectional area of the visceral fat 10 and subcutaneous fat 8 on or around the cross section where the electrodes are arranged.

Figure 15:
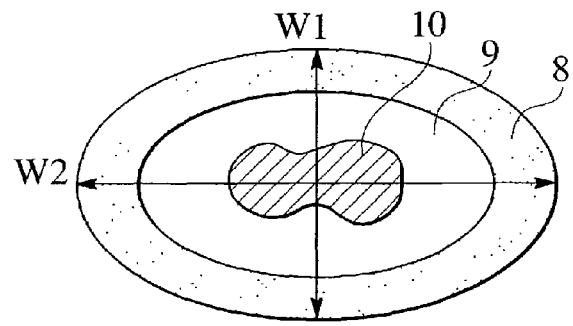
FIG. 15 shows the longitudinal and lateral widths of a human body as examples of characteristic quantities representing the size of the human body.

The characteristic quantity representing the size of the subject is, a value related to the size of the cross section of the subject. It may be a total cross-sectional area S, a circumferential length U around a cross section of the subject, a longitudinal width W1, or a lateral width W2 shown in FIG. 15. A power of the characteristic quantity representing the size of the subject is typically the first power of the total cross-sectional area S, the product W1·W2 of the longitudinal and lateral widths, or the second power $U^2$ of the circumferential length U. In practice, it is difficult to correctly measure the total cross-sectional area S, and therefore, W1·W2 and $U^2$ that are highly correlative with S are used. It is also possible to use values having integral exponents, such as W1, W2, and U having an exponent of 1, $W1^2$, $W2^2$, W1·U, and W2·U having an exponent of 2, $U^3$ and W1·W2·U having an exponent of 3, and $U^4$ having an exponent of 4. It is also possible to employ values having non-integral exponents, such as $U^{1.8}$ and $U^{2.2}$. Weighted linear sums or differences of such values are also usable. The characteristic quantity representing the size of the subject may be a quantity indirectly representing the cross-sectional area of the subject such as the weight of the subject or the ratio of the weight to the height of the subject.

To compute the quantity of the visceral fat 10, it is necessary to prepare a correlation expression to correlate the cross-sectional area m of the visceral fat 10 with the product $\zeta \times W1 \times W2$, or $\zeta \times U^2$ of the spatial potential gradient $\zeta$ and the second power of a characteristic quantity representing the size of the subject 1. The correlation expression can be approximated with a linear polynomial based on a multivariate analysis. The approximated correlation expression is, for example, $m = a0 + a1 \cdot \zeta \cdot W1 \cdot W2$, or $m = a0 + a1 \cdot \zeta \cdot U^2$, where a0 and a1 are regressive coefficients. Also possible are $m = a0 + a1 \cdot \zeta \cdot W1 \cdot W2 + a2 \cdot W1 \cdot W2$, and $m = a0 + a1 \cdot \zeta \cdot U^2 + a2 \cdot U^2$, where a2 is a regressive coefficient. Another voltage V' measured in another current path on the subject 1 may be employed to provide correlation expressions of improved accuracy, such as $m = a0 + a1 \cdot \zeta \cdot W1 \cdot W2 + a2 \cdot V' \cdot W1 \cdot W2$, and $m = a0 + a1 \cdot \zeta \cdot U^2 + a2 \cdot V' \cdot U^2$. Values related to the characteristic quantity representing the size of the subject 1 may be other than W1·W2 and $U^2$. Such values are replaced with W1·W2 or $U^2$ in the correlation expressions. If the distance L12 between the electrodes 21 and 22 is changed in proportion to the circumferential length U in FIG. 10, the voltage |V1−V2| may be employed instead of the spatial potential gradient $\zeta$. In this case, the correlation expression will be $m = a0 + a1 \cdot |V1-V2| \cdot W1 \cdot W2$, or $m\ a0 + a1 \cdot |V1-V2| \cdot U^2$. Once the correlation expression is set, the visceral fat quantity m of a given sample is calculable from a spatial potential gradient $\zeta$ or voltage |V1−V2| measured on the sample and a characteristic quantity representing the size of the sample.

Figure 16:
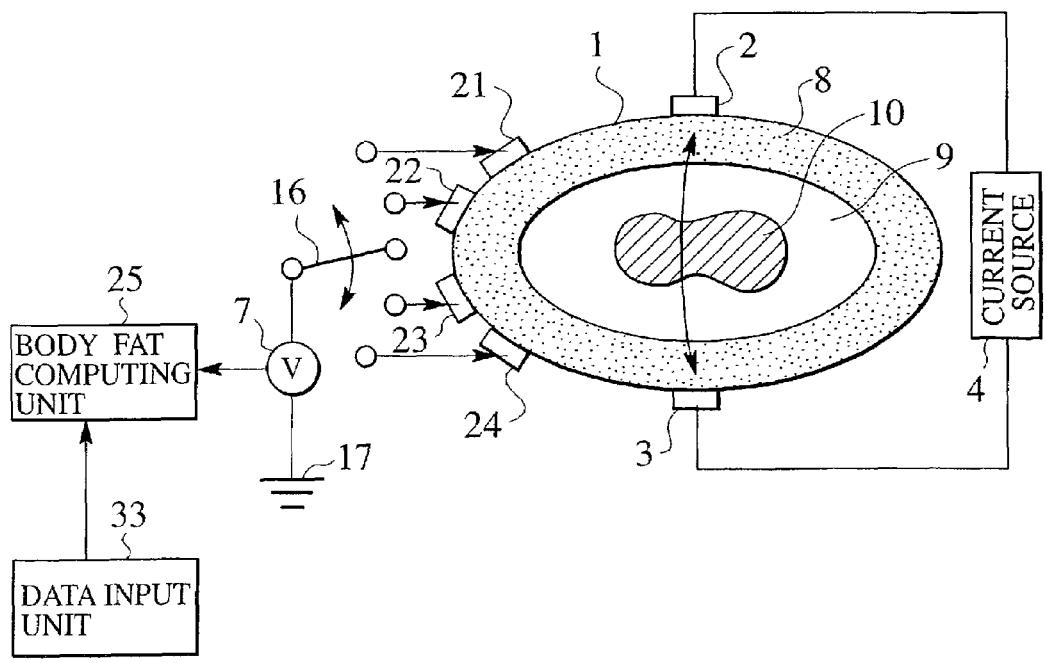
FIG. 16 shows a body fat measuring apparatus according to a second embodiment based on the second aspect.

The second embodiment will be explained. FIG. 16 shows a body fat measuring apparatus according to the second embodiment. The apparatus has two current electrodes 2 and 3 arranged substantially opposite to each other across a subject 1, a current source 4, measuring electrodes 21 to 24 arranged on a circumference of the subject 1 substantially at an intermediate position between the electrodes 2 and 3, a distance between adjacent ones of the electrodes being sufficiently shorter than the circumferential length of the subject 1, a reference potential 17 to measure potential of the measuring electrodes 21 to 24, a switch 16 to connect the reference potential 17 to the measuring electrodes 21 to 24, a voltmeter 7 to measure potential of the four measuring electrodes 21 to 24, a data input unit 33 to enter a circumferential length U of the subject 1 and positional data concerning the measuring electrodes, and a body fat computing unit 25 to compute the quantity of visceral fat 10 in the subject 1 according to the voltages measured with the voltmeter 7 and the circumferential length U and electrode positional data entered through the data input unit 33. The current electrodes 2 and 3 may be arranged on the back and abdomen of the subject 1, respectively, or on the flanks of the subject 1, respectively. To accurately measure a visceral fat quantity, it is preferable that the electrodes 2 and 3 are arranged on the back and abdomen of the subject 1, respectively.

A body fat measuring method will be explained. The current source 4 passes a current between the current electrodes 2 and 3 that are arranged on a circumference of the subject 1 substantially opposite to each other across the subject 1. The switch 16 is switched so that the voltmeter 7 measures voltages V1 to V4 between the measuring electrodes 21 to 24 and the reference potential 17. The body fat computing unit 25 computes a spatial potential gradient $\zeta$ according to the voltages V1 to V4 measured with the voltmeter 7 and the circumferential length U and electrode positional data entered through the data input unit 33 and calculates a quantity m of the visceral fat 10 according to the spatial potential gradient ζ.

Figure 17:
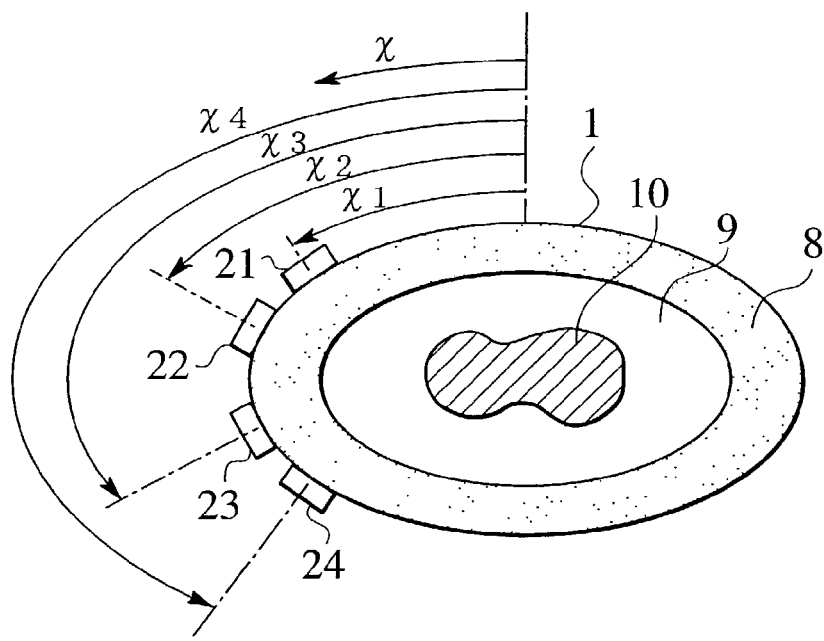
FIG. 17 shows the locations of measuring electrodes each expressed with a distance from a point on a human body to the center of the measuring electrode.
Figure 18:
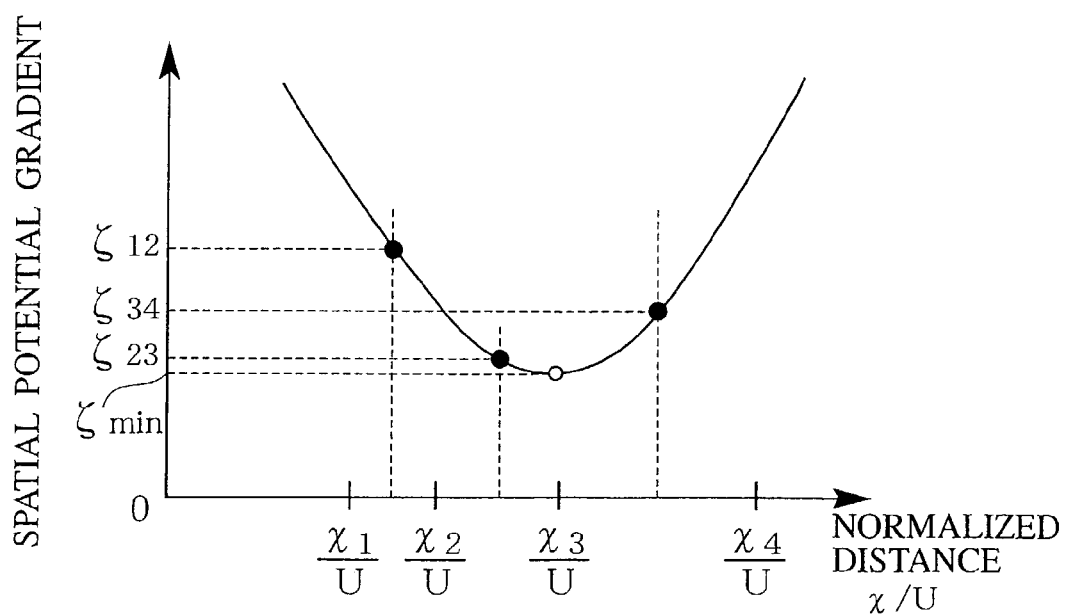
FIG. 18 shows a correlation between normalized distance and spatial potential gradient.

Calculating the spatial potential gradient ζ from the voltages V1 to V4 will be explained. FIG. 17 shows the positions χ1, χ2, χ3, and χ4 of the measuring electrodes 21, 22, 23, and 24, these positions corresponding to the distances from a point on the surface of the subject 1 to the centers of the electrodes. This electrode positional data is entered through the data input unit 33. The body fat computing unit 25 uses the data pieces χ1 to χ4 entered through the data input unit 33 and calculates the distance L12=χ2−χ1 between the electrodes 21 and 22, the distance L23=χ3−χ2 between the electrodes 22 and 23, and the distance L34=χ4−χ3 between the electrodes 23 and 24. Based on them, the body fat computing unit 25 computes local spatial potential gradients between the electrodes as ζ12= |V1−V2|·U/L12, ζ23=|V2−V3|·U/L23, and ζ34=|V3−V4|·U/ L34. The simplest way to find the spatial potential gradient ζ is to calculate an arithmetic average of the local spatial potential gradients ζ12, ζ23, and ζ34. Alternatively, the spatial potential gradient ζ may be the smallest one among ζ12, ζ23, and ζ34. The spatial potential gradient ζ may also be obtained, as shown in FIG. 18, by plotting ζ12 at x/U=(χ1+χ2)/2U, ζ23 at x/U=(χ2+χ3)/ 2U, and ζ34 at x/U=(χ3+χ4)/2U, fitting these three points to a quadratic function, finding a minimal value ζmin of the quadratic function, and defining the minimal value as the spatial potential gradient ζ.

Based on the spatial potential gradient ζ thus obtained, a visceral fat quantity or a total fat quantity (the sum of visceral and subcutaneous fat quantities) is computed in the same manner as the first embodiment.

Figure 19:
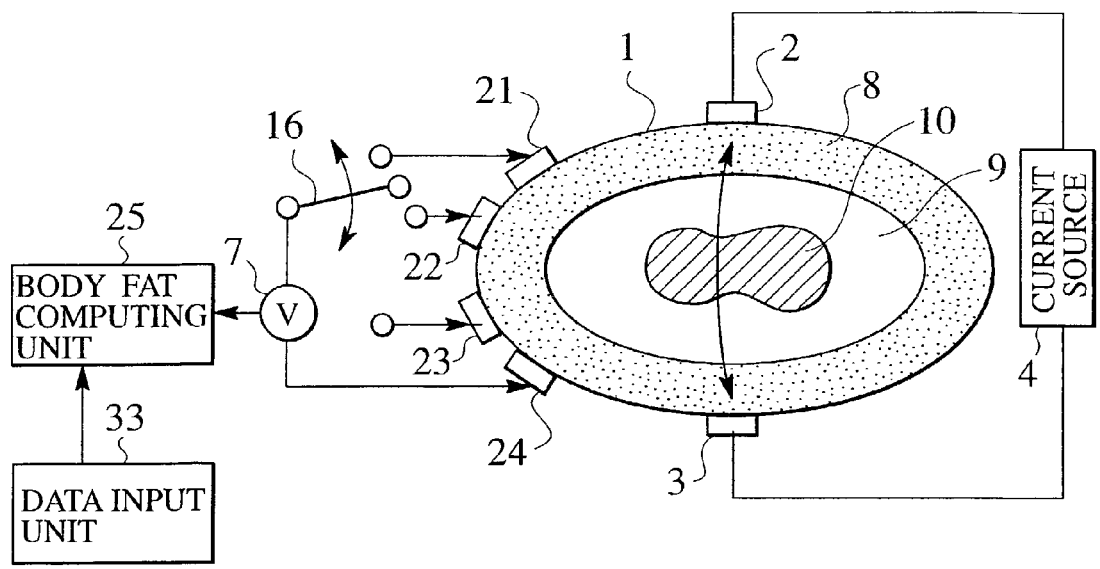
FIG. 19 shows a body fat measuring apparatus according to a third embodiment based on the second aspect.

The third embodiment will be explained. FIG. 19 shows a body fat measuring apparatus according to the third embodiment. This apparatus sets the reference potential 17 of the body fat measuring apparatus of FIG. 16 to an electrode 24 on a subject 1. In FIG. 19, a switch 16 connects the reference measuring electrode 24 to one of measuring electrodes 21 to 23. A voltmeter 7 measures voltages generated between the reference measuring electrode 24 and the measuring electrodes 21 to 23.

A body fat measuring method carried out with the apparatus of FIG. 19 will be explained. A current source 4 passes a current between current electrodes 2 and 3. The switch 16 is operated so that the voltmeter 7 may measure voltages V1 to V3 between the reference measuring electrode 24 and the measuring electrodes 21 to 23. A body fat computing unit 25 uses the voltages V1 to V3 measured with the voltmeter 7 and a circumferential length U and electrode position data entered through a data input unit 33, to find a spatial potential gradient ζ and compute a quantity m of visceral fat 10 from the spatial potential gradient ζ.

Finding the spatial potential gradient ζ from the voltages V1 to V3 is achieved like the second embodiment by replacing the spatial potential gradient ζ34 of the second embodiment with V3·U/L34. Using the spatial potential gradient ζ thus determined and the method of the first embodiment, the visceral fat quantity or a total fat quantity (the sum of visceral and subcutaneous fat quantities) is calculated.

Figure 20:
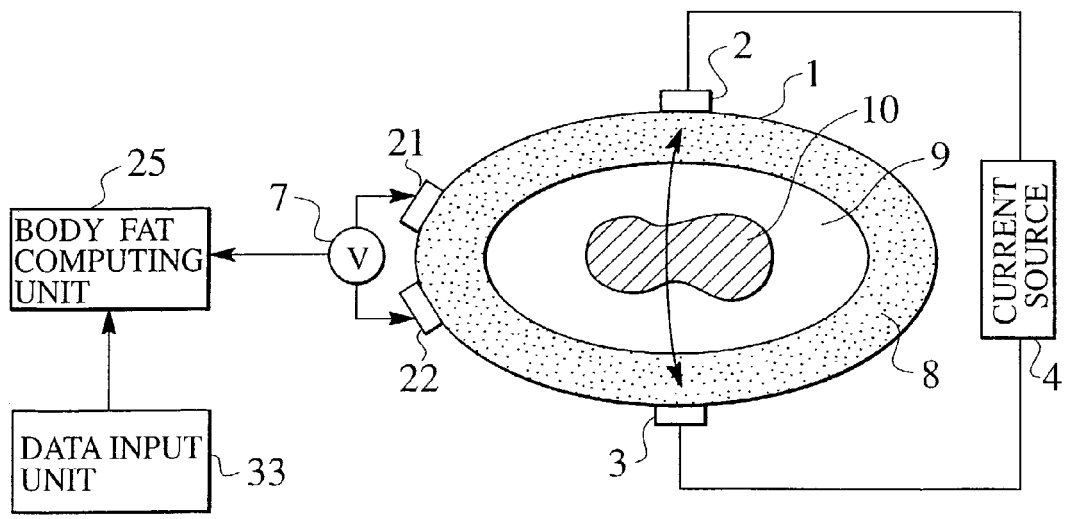
FIG. 20 shows a body fat measuring apparatus according to a fourth embodiment based on the second aspect.

The fourth embodiment will be explained. FIG. 20 shows a body fat measuring apparatus according to the fourth embodiment. This apparatus sets the reference potential 17 of the body fat measuring apparatus of FIG. 10 to an electrode 22 on a subject 1. A voltmeter 7 measures a voltage V generated between the reference measuring electrode 22 and a measuring electrode 21.

A body fat measuring method carried out with the apparatus of FIG. 20 will be explained. A current source 4 passes a current between current electrodes 2 and 3. The voltmeter 7 measures a voltage V between the measuring electrode 21 and the reference measuring electrode 22. A body fat computing unit 25 computes a quantity m of visceral fat 10 according to the voltage V measured with the voltmeter 7. More precisely, the voltage |V1−V2| of the first embodiment is replaced with the voltage V, and the same method as that of the first embodiment is employed to compute the visceral fat quantity or a total fat quantity (the sum of visceral and subcutaneous fat quantities).

Figure 21A:
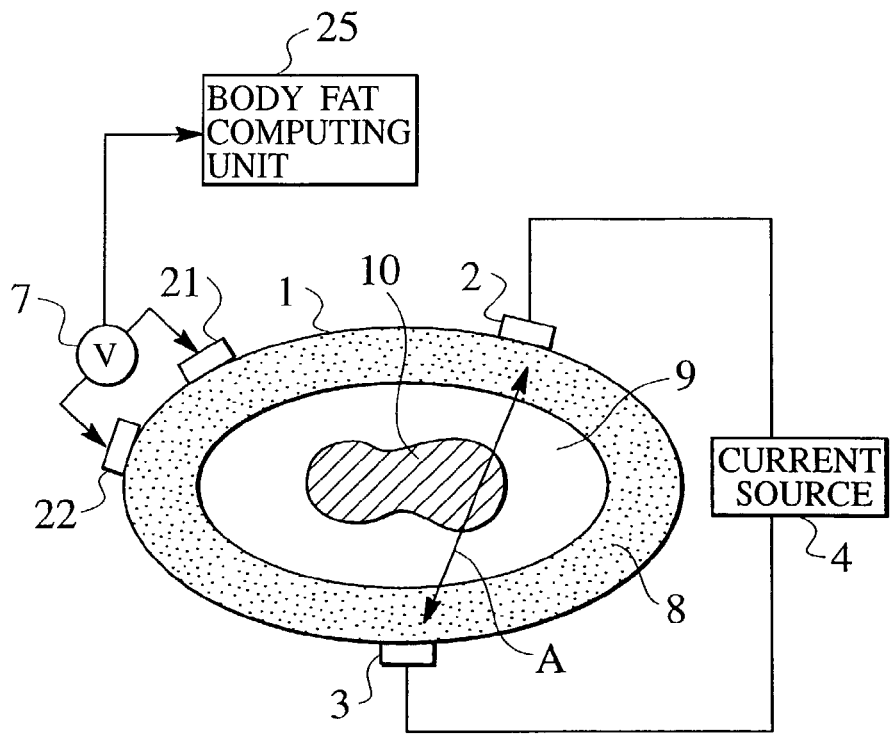
FIGS. 21A and 21B show a body fat measuring apparatus according to a fifth embodiment based on the second aspect.
Figure 21B:
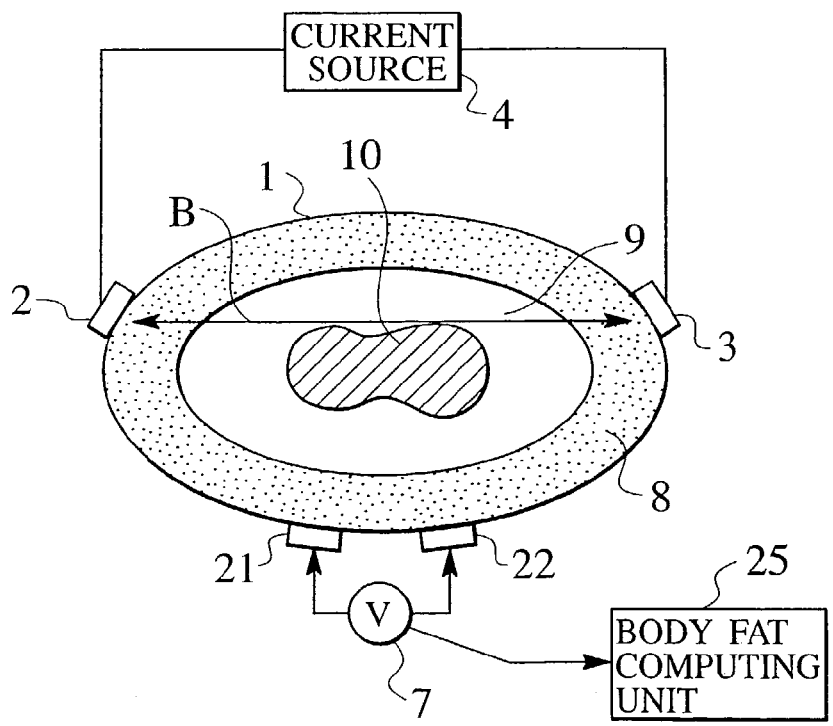

The fifth embodiment will be explained. FIG. 21A shows a body fat measuring apparatus according to the fifth embodiment. Current electrodes 2 and 3 are arranged substantially opposite to each other across a subject 1 and are oriented in a first direction depicted by "A". A current source 4 passes a current between the current electrodes 2 and 3. Measuring electrodes 21 and 22 are arranged substantially at an intermediate position between the current electrodes 2 and 3. A voltmeter 7 measures a voltage generated between the measuring electrodes 21 and 22. FIG. 21B shows another body fat measuring apparatus. Current electrodes 2 and 3 are arranged substantially opposite to each other across the subject 1 and are oriented in a second direction depicted by "B". A current source 4 passes a current between the current electrodes 2 and 3. Measuring electrodes 21 and 22 are arranged substantially at an intermediate position between the current electrodes 2 and 3. A voltmeter 7 measures a voltage generated between the measuring electrodes 21 and 22.

In this way, currents are successively supplied in a plurality of directions across the subject 1, and voltages generated by the currents are measured. According to the voltages, a body fat computing unit 25 precisely computes the quantity of visceral fat 10 in the subject 1.

This measuring method needs a correlation expression to correlate the measured n voltages (V1 to Vn) with the visceral fat quantity m. The correlation expression may be prepared like the first embodiment. The correlation expression may be approximated by a linear polynomial based on a multivariate analysis, such as m=a0+a1·V1+a2·V2+ . . . +an·Vn, where a0 to an are regression coefficients. Once the correlation expression is prepared, it is possible to calculate the quantity m of visceral fat of a sample from a set of voltages (V1 to Vn) measured on the sample. The correlation expression may be prepared according to a set of values (V1·U/L1, V2·U/L2, . . . , Vn·U/Ln) obtained by multiplying the measured voltages Vi (i=1 to n) by a separately measured circumferential length U and dividing the products by distances Li (i=1 to n) between the measuring electrodes. The correlation expression makes it possible to calculate the quantity m of visceral fat of a sample from values (V1·U/L1, V2·U/L2, . . . , Vn·U/Ln) measured on the sample. The correlation expression may be prepared by using also the characteristic quantities of the subject 1 such as longitudinal width W1, lateral width W2, and circumferential length U. This correlation expression will be m=a0+(a1·V1·U/ L1+a2V2·U/L2+ . . . +an·Vn·U/Ln)·W1·W2, or m=a0+ (a1·V1·U/L1+a2·V2·U/L2+ . . . +an·Vn·U/Ln) ·U². This correlation expression is used to calculate a cross-sectional area m of the visceral fat 10.

The sixth embodiment will be explained. A body fat measuring apparatus according to the sixth embodiment is made by adding a measuring apparatus of FIG. 22A and/or that of FIG. 22B to the body fat measuring apparatus of FIG. 20, or by adding a measuring apparatus of FIG. 23A and/or that of FIG. 23B to the apparatus of FIG. 20. The measuring apparatuses of FIGS. 22A and 22B correspond to the measuring apparatus of FIG. 7A. The measuring apparatuses of FIGS. 23A and 23B correspond to the measuring apparatus of FIG. 1. Detailed explanations of them will be omitted.

A body fat measuring method will be explained. In the measuring apparatus of FIG. 20, the current source 4 passes a current between the current electrodes 2 and 3, and the voltmeter 7 measures a first voltage V generated between the measuring electrodes 21 and 22.

Figure 22A:
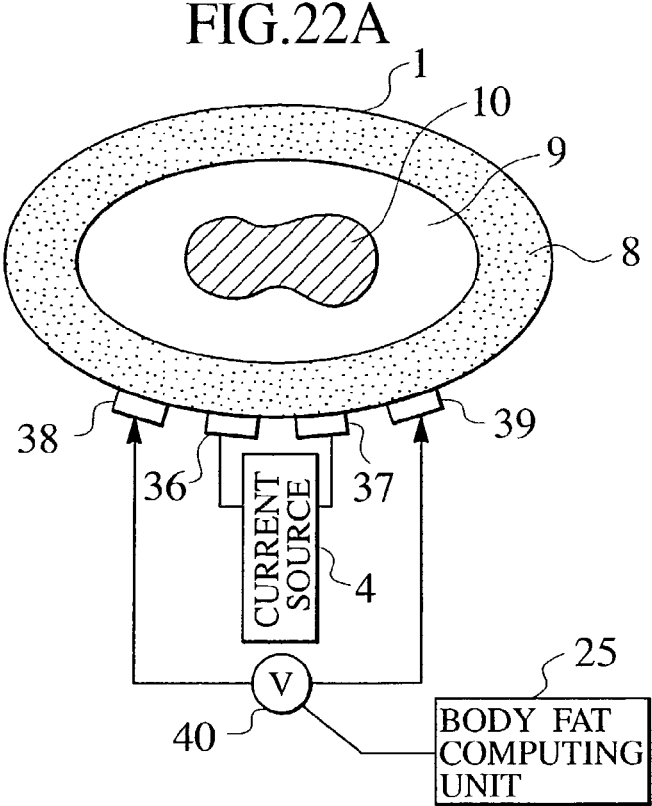
FIGS. 22A and 22B show a body fat measuring apparatus according to a sixth embodiment based on the second aspect.

In the measuring apparatus of FIG. 22A, a current source 4 passes a current between two current electrodes 36 and 37, and a voltmeter 40 measures a second voltage V' between two measuring electrodes 38 and 39. In the measuring apparatus of FIG. 22B, a current source 4 passes a current between two current electrodes 36' and 37', and a voltmeter 40 measures a second voltage V" between two measuring electrodes 38' and 39'. A body fat computing unit 25 uses the second voltages V' and V" measured with the voltmeters 40, to correct the first voltage V measured with the voltmeter 7, and computes the quantity of visceral fat 10 according to the corrected voltage.

Figure 22B:
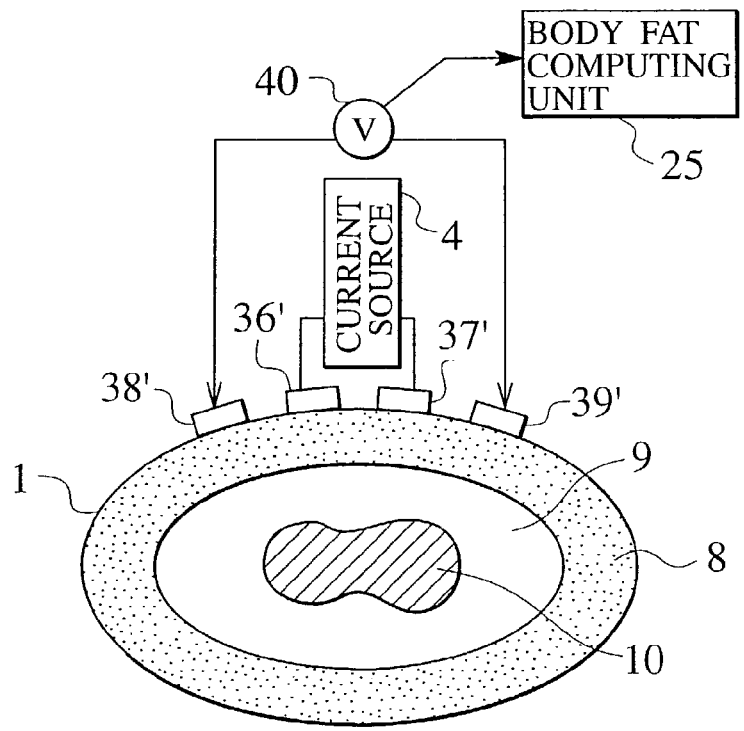

The voltage V measured with the voltmeter 7 includes the influence of a distribution of subcutaneous fat 8 of the subject 1, in particular, the influence of the thickness of the subcutaneous fat 8 around the electrodes 2 and 3. In FIG. 22B, the voltage (impedance) V" is measured by passing a current around the electrode 2, and in FIG. 22A, the voltage (impedance) V" is measured by passing a current around the electrode 3. Thus, these voltages V" and V' are used to remove the influence of the subcutaneous fat, to improve measuring accuracy. If it is known beforehand that the thickness of the subcutaneous fat 8 around the electrode 2 is substantially equal to that around the electrode 3, only one of the voltages V' and V" may be used to correct the voltage V measured with the voltmeter 7.

The correction of the voltage is carried out when preparing a correlation expression. That is, the ordinate of FIG. 14 is set to represent V−a'V'−a"V", and the coefficients a' and a" are properly set to provide a better correlation. The correlation expression may be approximated by a linear polynomial based on a multivariate analysis, such as $m=a0+a \cdot V-a' \cdot V'-a'' \cdot V''$, where a0, a, a', and a" are regressive coefficients to be determined.

A more general correction technique using the distance L12 between the electrodes 21 and 22 and the circumferential length U of the subject 1 may be employed. In this case, the ordinate of FIG. 14 is V·U/L12−a'·V'−a"·V". A correlation expression based on a multivariate analysis is, for example, $m=a0+a \cdot V \cdot U/L12-a' \cdot V'-a'' \cdot V''$. The circumference length U of the subject 1 and the second power $U^2$ thereof may be used as independent variables to provide a correlation expression of $m=a0+a \cdot V \cdot U \cdot L12-a' \cdot V'-a'' \cdot V''+a1/U+a2/U^2$, where a1 and a2 are regressive coefficients. This improves measuring accuracy.

A power of a characteristic quantity representing the size of the subject 1 may be employed to find a cross-sectional area m of the visceral fat 10. In this case, a correlation expression based on a multivariate analysis is, for example, $m=a0+a \cdot V \cdot (U/L12) \cdot \epsilon -a' \cdot V' \epsilon' -a'' \cdot V'' \cdot \epsilon''$, where $\epsilon$, $\epsilon'$, and $\epsilon''$ are exponential values of the characteristic quantity representing the size of the subject 1. For example, they are the product W1·W2 of a longitudinal width W1 and lateral width W2 of the subject 1, and the second power $U^2$ of the circumferential length U of the subject 1. Exponents are not limited to 1 and 2. They are determined to provide an optimum correlation. If $\epsilon$, $\epsilon'$, and $\epsilon''$ are each $U^2$, the correlation expression will be $m=a0+a \cdot V \cdot (U/L12) \cdot U^2-a' \cdot V' \cdot U^2-a'' \cdot V'' \cdot U^2$. When U and $U^2$ are used as independent variables, the correlation expression will be $m=a0+a \cdot V \cdot (U/L12) \cdot U^2-a' \cdot V' \cdot U^2-a'' \cdot V'' \cdot U^2+a1 \cdot U+a2 \cdot U^2$, to improve computation accuracy. When changing the distance L12 between the electrodes 21 and 22 in proportion to the circumferential length U, the correlation expression is $m=a0+a \cdot V \cdot \epsilon -a' \cdot V' \cdot \epsilon -a'' \cdot V'' \cdot \epsilon''$, or $m=a0+a \cdot U^2-a' \cdot v' U^2-a'' \cdot ''' \cdot U+a1 \cdot U+a2 \cdot U^2$.

The above-mentioned example uses the measuring apparatuses of FIG. 22 to correct a voltage. Instead of the apparatus of FIG. 22A, the measuring apparatus of FIG. 23A may be employed, and instead of the measuring apparatus of FIG. 22B, the measuring apparatus of FIG. 23B may be employed. In this case, a voltage measured with a voltmeter 40 will not greatly vary even if the positions of electrodes 41 and 41' slightly shift. Thus, this arrangement makes it possible to accurately measure a voltage even if electrode positions slightly shift. This results in further correctly computing a visceral fat quantity. The current electrodes and measuring electrodes of FIG. 22 or FIG. 23 may be arranged at other locations along a circumference of the subject 1, to measure second voltages based on the measuring method of FIG. 22 or FIG. 23. The measured second voltages are used to correct the first voltage V, to further improve measuring accuracy. The measuring apparatus of FIG. 22 or FIG. 23 may be added to the measuring apparatus of any one of FIGS. 10, 11, 12, 16, and 19 instead of the apparatus of FIG. 20, to precisely measure a visceral fat quantity.

The seventh embodiment will be explained. A body fat measuring apparatus according to the seventh embodiment has the same structure as that of FIG. 8 and successively passes currents in different directions to automatically measure visceral fat in a subject 1. Through the data input unit 33, a correlation expression to correlate voltages with a visceral fat quantity m is entered into the computer 35. The computer 35 uses the correlation expression to find a visceral fat quantity m and provides the data output unit 34 with the visceral fat quantity m. The data output unit 34 displays the received data. The other parts and measuring operations of the seventh embodiment are the same as those of the fourth embodiment of the first aspect.

Selecting current electrodes and measuring electrodes will be explained. For example, the arrangements of FIGS. 20, 21A, and 21B are successively selected. The voltage correction process of FIG. 22 or of FIG. 23 may be additionally carried out in each direction, to remove the influence of the distribution and quantity of subcutaneous fat of the subject 1. This results in improving the computation accuracy of the quantity of the visceral fat 10.

The first to seventh embodiments may carry out measurements at different current frequencies and compare the measurement results with each other, to improve the reliability of the measurements.

Third Aspect

A method of and an apparatus for measuring body fat according to the third aspect measure a subcutaneous fat quantity such as the thickness or cross-sectional area of subcutaneous fat, a visceral fat quantity such as the cross-sectional area of visceral fat, or the sum of subcutaneous and visceral fat quantities.

Figure 24:
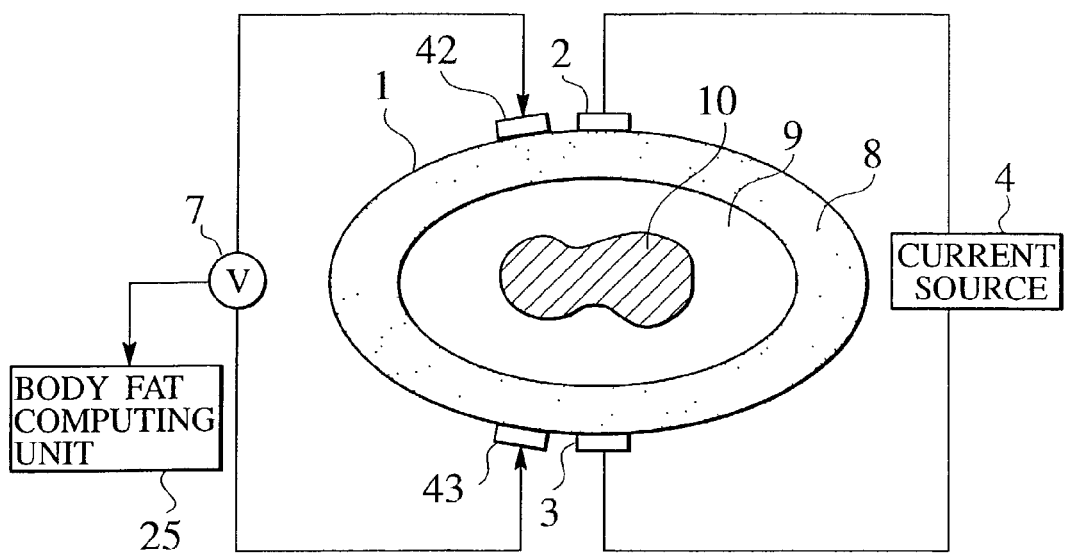
FIG. 24 shows a body fat measuring apparatus according to a first embodiment based on a third aspect.
Figure 25:
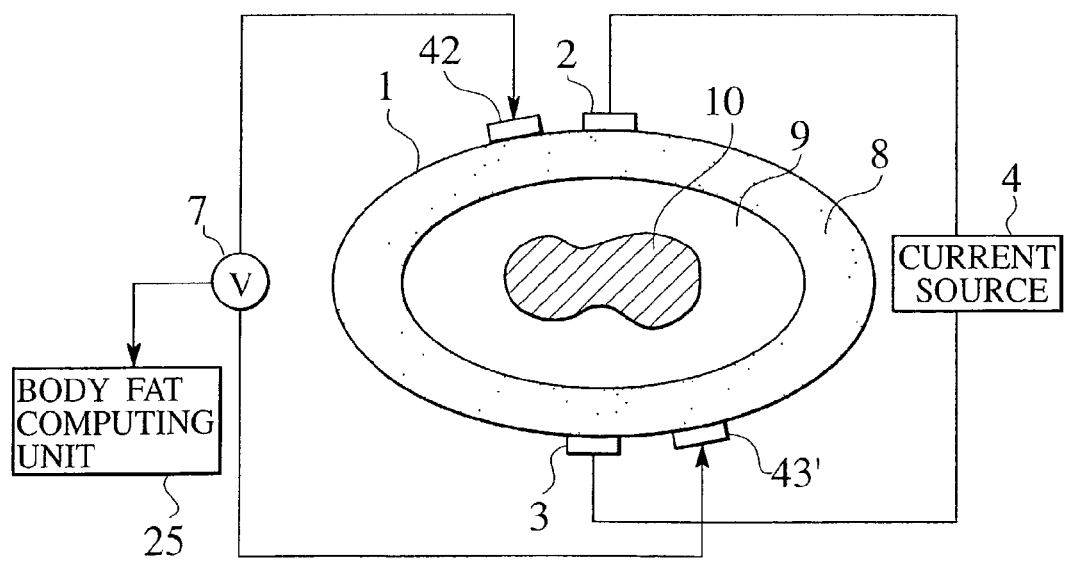
FIG. 25 shows another example of a body fat measuring apparatus according to the first embodiment based on the third aspect.
Figure 26:
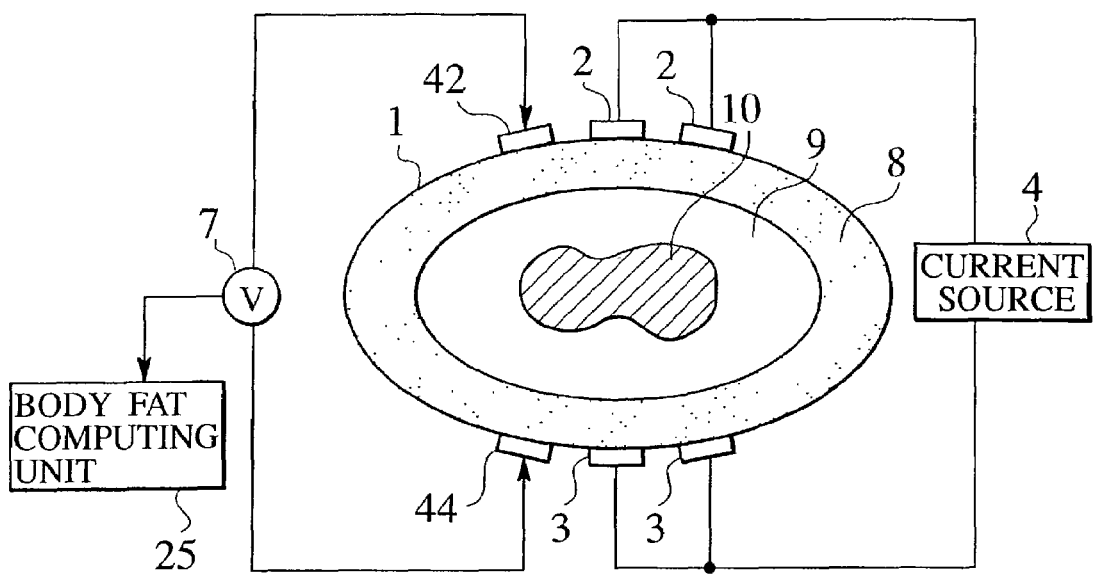
FIG. 26 shows another example of a body fat measuring apparatus according to the first embodiment based on the third aspect.

FIG. 24 shows a body fat measuring apparatus according to the first embodiment based on the third aspect. The apparatus has two current electrodes 2 and 3 arranged along a circumference of, for example, the body of a subject 1 approximately opposite to each other across the subject 1, a current source 4, a measuring electrode 42 arranged close to the electrode 2, a measuring electrode 43 arranged close to the electrode 3, a voltmeter 7 to measure a voltage generated between the two measuring electrodes 42 and 43, and a body fat computing unit 25 to compute the sum of a cross-sectional area of subcutaneous fat 8 and a cross-sectional area of visceral fat 10 of the subject 1 according to the voltage measured with the voltmeter 7. The current electrodes 2 and 3 may be arranged on the back and abdomen of the subject 1, respectively, or on the flanks of the subject 1, respectively. To accurately measure a fat quantity, it is preferable that they are arranged on the back and abdomen of the subject 1, respectively. The measuring electrode adjacent to the electrode 3 may be arranged at a position substantially symmetrical to the electrode 43 across the electrode 3, as shown in FIG. 25. The number of current electrodes arranged along a circumference of the subject 1 may be greater than 2 as shown in FIG. 26, if the electrodes can pass a current across the subject 1.

A body fat measuring method will be explained. In the measuring apparatus of FIG. 24, the current source 4 passes a current between the current electrodes 2 and 3. The voltmeter 7 measures a voltage V generated between the measuring electrodes 42 and 43. The body fat computing unit 25 uses the voltage V measured with the voltmeter 7, to compute the sum m' of a cross-sectional area of the subcutaneous fat 8 and a cross-sectional area of the visceral fat 10 in the subject 1. A person having a large total fat quantity (the sum of subcutaneous and visceral fat quantities) generally has a large visceral fat quantity. The voltage V, therefore, is usable to compute a cross-sectional area m of the visceral fat 10 of the subject 1.

The current source 4 has already been explained in the first aspect, and therefore, the explanation thereof will be omitted.

It is easily expected that a voltage generated when a current is passed substantially across the subject 1, as shown in FIG. 24, has some correlation with a fat quantity that mainly causes electric resistance in the subject 1. It is surprising however that the voltage V accurately reflects the ratio (relative value) of the sum of a cross-sectional area of the subcutaneous fat 8 and a cross-sectional area of the visceral fat 10 of the subject 1 to a total cross-sectional area of the subject 1 at or around a cross section around which the electrodes are arranged. It is also beyond expectation that the product obtained by multiplying the voltage by a power of a characteristic quantity representing the size of the subject 1 shows a strong correlation with the sum (absolute value) of the cross-sectional area of the subcutaneous fat 8 and the cross-sectional area of the visceral fat 10 at the cross section in question. The characteristic quantity representing the size of the subject and a power thereof have been explained in the first embodiment of the second aspect.

To compute the sum m' of the subcutaneous fat 8 and visceral fat 10, it is necessary to prepare a correlation expression to correlate the voltage V with the fat quantity m'. Alternatively, it is necessary to prepare a correlation expression to correlate the product of the voltage V and a power of the characteristic quantity representing the size of the subject 1, for example, $V \times W1 \times W2$, or $V \times U^2$ with the fat quantity m'. The correlation expression may be prepared like the first embodiment of the second aspect.

The correlation expression can be approximated by a linear polynomial based on a multivariate analysis. If the quantity m' indicates the ratio (relative value) of the sum of the cross-sectional areas of the subcutaneous fat 8 and visceral fat 10 to the total cross-sectional area of the subject 1, the expression will be, for example, $m'=a0+a \cdot V+a2 \cdot L/U$, where a0, a1, and a2 are regression coefficients and L is the distance between the electrodes 2 and 42, or 3 and 43. If the quantity m' indicates the sum (absolute value) of the cross-sectional areas of the subcutaneous fat 8 and visceral fat 10, the expression will be $m'= a0+a1 \cdot V \cdot W1 \cdot W2$, or $m'=a0+a1 \cdot V \cdot U^2$. The values $W1 \cdot W2$ and $U^2$ may be used as independent variables to provide $m'=a0+a1 \cdot V \cdot W1 \cdot W2+a2 \cdot W1 \cdot W2+a3 \cdot W1 \cdot W2 \cdot L/U$, or $m'=a0+a1 \cdot V \cdot U+a2 \cdot U^2+a3 \cdot U^2 \cdot L/U$, where a3 is a regression coefficient. This improves the accuracy of the correlation expression. The exponential values of the characteristic quantity representing the size of the subject 1 are not limited to $W1 \cdot W2$ and $U^2$. If other exponential values are employed, they are replaced with $W1 \cdot W2$ and $U^2$. Once the correlation expression is set, the fat quantity m' of a sample is calculable from the correlation expression, a voltage V measured on the sample, and a characteristic quantity representing the size of the sample.

In FIG. 24, the distance between the current electrode 2 and the measuring electrode 42 must be in a proper range. If the distance is too large, a voltage drop due to the subcutaneous fat 8 less occupies the measured voltage V, to deteriorate measuring accuracy. In addition, measuring sensitivity will be poor on samples having thin subcutaneous fat. If the distance is too small, measuring sensitivity will be poor on samples having thick subcutaneous fat. In addition, the shapes and sizes of the electrodes and contact states between the electrodes and the subject 1 will affect the measured voltage V. The distance between the electrodes 2 and 42 is preferably 0.3 to 3 times the thickness of the subcutaneous fat 8. When arranging the electrodes along a circumference of the waist of a human body, the distance (center-to-center distance) between the electrodes 2 and 42 is preferably 0.6 cm to 12 cm, more preferably, 1 cm to 6 cm. The distance between the electrodes 2 and 42 may be changed in proportion to the circumferential length U of a subject. Changing the distance between the electrodes in proportion to a circumferential length is achievable by fixing the electrodes on a belt made of elastic material such as rubber and winding the belt around a subject so that the belt may expand and contract on the subject. The same is applicable to the distance between the current electrode 3 and the measuring electrode 43.

The shapes of the current electrodes and measuring electrodes are, for example, disks or rectangles. If disk electrodes are employed, they may have a diameter of 0.6 cm to 3.5 cm, preferably, 1.5 cm to 2.5 cm.

Figure 27:
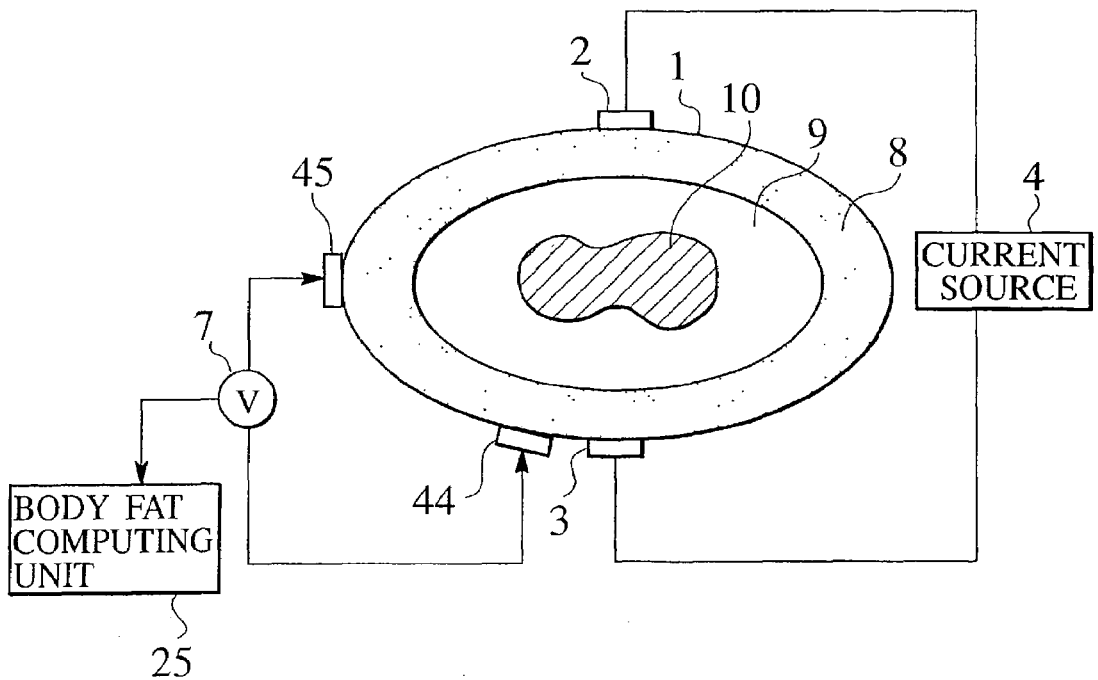
FIG. 27 shows a body fat measuring apparatus according to a second embodiment based on the third aspect.

The second embodiment will be explained. FIG. 27 shows a body fat measuring apparatus according to the second embodiment. The apparatus has two current electrodes 2 and 3 arranged along a circumference of, for example, the body of a subject 1 substantially opposite to each other across the subject 1, a current source 4, a measuring electrode 44 arranged close to the electrode 3, a measuring electrode 45 arranged on the circumference of the subject 1 substantially at an intermediate position between the two current electrodes 2 and 3, a voltmeter 7 to measure a voltage generated between the two measuring electrodes 44 and 45, and a body fat computing unit 25 to compute the sum of a cross-sectional area of subcutaneous fat 8 and a cross-sectional area of visceral fat 10 in the subject 1 according to the voltage measured with the voltmeter 7. The current electrodes 2 and 3 may be arranged on the back and abdomen of the subject 1, respectively, or on the flanks of the subject 1, respectively. To accurately measure a fat quantity, it is preferable that they are arranged on the back and abdomen of the subject 1, respectively. The distance between the current electrode 3 and the measuring electrode 44 is set in a proper range like the distance between the current electrode 2 and the measuring electrode 42 of FIG. 24.

A body fat measuring method will be explained. In the measuring apparatus of FIG. 27, the current source 4 passes a current between the current electrodes 2 and 3. The voltmeter 7 measures a voltage V generated between the measuring electrodes 44 and 45. The body fat computing unit 25 uses the voltage V measured with the voltmeter 7, to compute the sum m' of a cross-sectional area of the subcutaneous fat 8 and a cross-sectional area of the visceral fat 10 in the subject 1. A person having a large total fat quantity (the sum of subcutaneous and visceral fat quantities) generally has a large visceral fat quantity. The voltage V, therefore, is usable to compute the cross-sectional area m of the visceral fat 10 of the subject 1.

To compute the sum m' of the subcutaneous fat 8 and visceral fat 10, it is necessary to prepare a correlation expression to correlate the voltage V with the fat quantity m'. Alternatively, it is necessary to prepare a correlation expression to correlate the product of the voltage V and a power of a characteristic quantity representing the size of the subject 1, for example, V×W1×W2, or V×U$^2$ with the fat quantity m'. The correlation expression may be prepared like the first embodiment. In the correlation expression of the first embodiment, L is redefined as the distance between the electrodes 3 and 44. This correlation expression makes it possible to compute the fat quantity m' of a sample according to a voltage V measured on the sample and a characteristic quantity representing the size of the sample.

The third embodiment will be explained. A body fat measuring apparatus of the third embodiment is made by adding the body fat measuring apparatus of FIG. 1 to the body fat measuring apparatus of FIG. 24. The apparatuses have already been explained in the first embodiment of the third aspect and the first embodiment of the first aspect, and therefore, will not be explained again.

A body fat measuring method will be explained. In the measuring apparatus of FIG. 24, the current source 4 passes a current between the current electrodes 2 and 3. The voltmeter 7 measures a first voltage V generated between the measuring electrodes 42 and 43. In the measuring apparatus of FIG. 1, the current source 4 passes a current between the current electrodes 2 and 3. The voltmeter 7 measures a second voltage V' generated between the measuring electrodes 5 and 11. The body fat computing unit 25 uses the first and second voltages V and V' measured with the voltmeters 7, to compute the sum m' of a cross-sectional area of the subcutaneous fat 8 and a cross-sectional area of visceral fat 10 in a subject 1. The first voltage V is corrected by the second voltage V', to improve the computation accuracy of the fat quantity m'.

To compute the sum m' of the subcutaneous fat 8 and visceral fat 10, it is necessary to prepare a correlation expression to correlate the first and second voltages V and V' with the fat quantity m'. The correlation expression can be approximated by a linear polynomial based on a multivariate analysis. If the quantity m' indicates the ratio (relative value) of the sum of the cross-sectional areas of the subcutaneous fat 8 and visceral fat 10 to a total cross-sectional area of the subject 1, the expression will be, for example, m'=a0+a1·V+a2·V'+a3·L1/U+a4·L2/U+a5·L2'/U+a6·L2 L2'/U$^2$, where a0 to a6 are regression coefficients, L1 is the distance between the electrodes 2 and 42, or 3 and 43 of FIG. 24, L2 is the distance between the electrodes 2 and 3 of FIG. 1, and L2' is the distance between the electrodes 2 and 5 of FIG. 1. If the quantity m' indicates the sum (absolute value) of the cross-sectional areas of the subcutaneous fat 8 and visceral fat 10, the expression will be m'=a0+a1·V·ϵ+a2·V'·ϵ', or to further improve accuracy, m'=a0+a1·V·ϵ+a2·V'·ϵ'+(a3+a4·L1/U)·ϵ+(a5+a6·L2/U+a7·L2'/U+a8·L2·L2'/U$^2$)·ϵ', where a0 to a8 are regression coefficients and ϵ and ϵ' are exponential values of characteristic quantities representing the size of the subject 1, e.g., the product W1·W2 of a longitudinal width W1 and lateral width W2 of the subject and the second power U$^2$ of a circumferential length U of the subject. Exponents are not limited to 1 and 2 and are determined to optimize the correlation. Once the correlation expression is determined, it is used to compute the fat quantity m' of a sample according to voltages V and V' measured on the sample and characteristic quantities representing the size of the sample.

According to the body fat measuring apparatus of this embodiment, the current electrodes and measuring electrodes of FIG. 1 may be arranged at other locations along a circumference of the subject 1. In this case, second voltages are measured like the measuring method of FIG. 1, and the measured second voltages are used to correct the first voltage V, to further improve measuring accuracy.

The body fat measuring apparatus of this embodiment may additionally be provided with the body fat measuring apparatus of FIG. 7B. The voltmeter 15 of the body fat measuring apparatus of FIG. 7B measures a third voltage V", which is used to precisely compute the sum m' of the cross-sectional areas of the subcutaneous fat 8 and visceral fat 10 in the subject 1. If the quantity m' indicates the sum (absolute value) of the cross-sectional areas of the subcutaneous fat 8 and visceral fat 10, a correlation expression to be prepared is, for example, m'=a0+a·V·ϵ+a'·V'·ϵ'+a"·V"·ϵ", where a0, a, a', and a" are regression coefficients and ϵ, ϵ', and ϵ" are exponential values of characteristic quantities representing the size of the subject 1. Alternatively, the body fat measuring apparatus of FIG. 24 may additionally be provided with the body fat measuring apparatus of FIG. 7A and/or that of FIG. 7B, to compute the fat quantity m' in a similar manner. Instead of the body fat measuring apparatus of FIG. 24, the body fat measuring apparatus of FIG. 27 may be employed, to similarly compute the fat quantity m'.

The fourth embodiment will be explained. A body fat measuring apparatus according to the fourth embodiment has the same structure as the apparatus of FIG. 8, successively supplies currents in a plurality of directions, and computes the sum m' of a cross-sectional area of subcutaneous fat 8 and a cross-sectional area of visceral fat 10 in a subject 1. The data input unit 33 enters a correlation expression to correlate a voltage with a fat quantity m' into the computer 35 in advance. The computer 35 employs the correlation expression to find a body fat quantity m', which is transferred to the data output unit 34. The data output unit 34 displays the fat quantity m'. The other parts and measurement method of this embodiment are the same as those of the fourth embodiment of the first aspect.

The selection and arrangement of current electrodes and measuring electrodes are, for example, those shown in FIG. 24, or those shown in FIG. 27. The electrode arrangement of FIG. 1, FIG. 7A, or FIG. 7B is also employable. In this case, measured voltages are used in the above-mentioned correction operation in each direction, to precisely measure the sum m' of the cross-sectional areas of the subcutaneous fat 8 and visceral fat 10.

Figure 28:
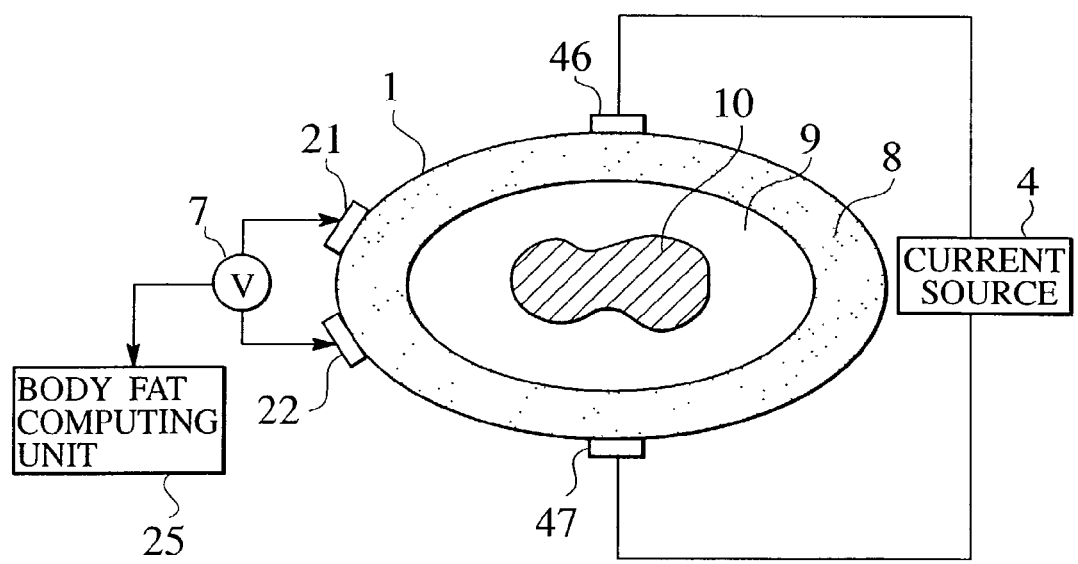
FIG. 28 shows a body fat measuring apparatus according to a fifth embodiment based on the third aspect.

A body fat measuring apparatus according to the fifth embodiment consists of the measuring apparatus of FIG. 24 and the measuring apparatus of FIG. 28. The body fat computing unit 25 uses a first voltage measured with the voltmeter 7 of FIG. 24 and a second voltage measured with the voltmeter 7 of FIG. 28, to compute the quantity of subcutaneous fat 8 of a subject 1. The measuring apparatus of FIG. 28 has the same structure as the measuring apparatus of FIG. 6 or FIG. 20. The measuring apparatus of FIG. 24 has already been explained in the first embodiment of the third aspect, and therefore, will not be explained in detail. The electrodes 2 and 46 may be the same electrode, and the electrodes 3 and 47 may be the same electrode. Instead of the body fat measuring apparatus of FIG. 24, any one of the body fat measuring apparatuses of FIGS. 25 and 26 is employable.

A body fat measuring method will be explained. In the measuring apparatus of FIG. 24, the current source 4 passes a current between the first and second current electrodes 3 and 2, and the voltmeter 7 measures a first voltage generated between the first and second measuring electrodes 43 and 42. In the measuring apparatus of FIG. 28, the current source 4 passes a current between the third and fourth current electrodes 47 and 46, and the voltmeter 7 measures a second voltage generated between the third and fourth measuring electrodes 21 and 22. The body fat computing unit 25 uses the first and second voltages measured with the voltmeters 7 to compute the quantity of the subcutaneous fat 8 of the subject 1. The quantity of the subcutaneous fat 8 may be the sum d+d' of the thickness d of subcutaneous fat around the electrode 3 and the thickness d' of subcutaneous fat around the electrode 2, or a cross-sectional area S of the subcutaneous fat at or around a cross section where the electrodes are arranged. The first voltage is substantially the sum of a voltage drop caused by the subcutaneous fat 8 around the electrodes 3 and 2 and a voltage drop caused by the visceral fat 10. The second voltage mainly corresponds to a voltage drop caused by the visceral fat 10. Therefore, subtracting the second voltage from the first voltage precisely provides the sum of the thickness of the subcutaneous fat 8 around the electrode 3 and the thickness of the subcutaneous fat 8 around the electrode 2. The difference between the first and second voltages may approximately provide a cross-sectional area of the subcutaneous fat 8.

To calculate the sum d+d' of the thickness d of the subcutaneous fat 8 around the current electrode 3 and the thickness d' of the same around the current electrode 2, a correlation expression to correlate the first and second voltages V1 and V2 with the subcutaneous fat thickness d+d' is prepared in advance. The correlation expression is approximated by a linear polynomial based on a multivariate analysis. If the quantity d+d' is the absolute value of the thickness of the subcutaneous fat 8, the correlation expression is, for example, $d+d'=a0+a1 \cdot V1 \cdot \epsilon1 - a2 \cdot (V2 \cdot U/L2) \cdot \epsilon2 + a3 \cdot \epsilon1 + a4 \cdot (L1/U) \cdot \epsilon1$, where a0, a1, a2, a3, and a4 are regression coefficients, L1 is the distance between the electrodes 2 and 42, or 3 and 43, L2 is the distance between the electrodes 21 and 22, and $\epsilon1$ and $\epsilon2$ are exponential values of characteristic quantities representing the size of the subject 1. For example, they are the first power of a circumferential length U of the subject 1, or a longitudinal width W1 or lateral width W2 of the subject 1. The exponent is not limited to 1 and may be determined to optimize the correlation. The electrode-to-electrode distances L1 and L2 may be changed in proportion to the circumferential length U of the subject 1. In this case, the correlation expression will be $d+d'=a0+a1 \cdot V1 \cdot \epsilon1 - a2 \cdot V2 \cdot \epsilon2 + a3 \cdot \epsilon1$.

To compute a cross-sectional area S of the subcutaneous fat 8, a correlation expression to correlate the first and second voltages V1 and V2 with the cross-sectional area S of the subcutaneous fat is prepared in advance. If the quantity S is the absolute value of the cross-sectional area of the subcutaneous fat 8, the correlation expression is, for example, $S=a0+a1 \cdot V \cdot \epsilon1 - a2 \cdot (V2 \cdot U/L2) \cdot \epsilon2 + a3 \cdot \epsilon1 + a4(L1/U)\epsilon1$, where $\epsilon1$ and $\epsilon2$ are typically the square $U^2$ of the circumferential length U of the subject 1, or the product W1·W2 of the longitudinal and lateral widths W1 and W2 across the subject 1. The electrode-to-electrode distances L1 and L2 may be changed in proportion to the circumferential length U of the subject 1. In this case, the correlation expression will be $S= a0+a1 \cdot V1 \cdot \epsilon1 - a2 \cdot V2 \cdot \epsilon2 + a3 \cdot \epsilon1$.

In FIG. 24, the distance between the first current electrode 3 and the first measuring electrode 43 and the distance between the second current electrode 2 and the second measuring electrode 42 are set as mentioned in the first embodiment of the third aspect. In FIG. 28, it is preferable that the distance between the third measuring electrode 21 and the fourth measuring electrode 22 is set like the distance between the electrodes 21 and 22 of FIG. 10 explained in the first embodiment of the second aspect.

According to this embodiment, the measuring apparatus of FIG. 28 can be replaced with the measuring apparatus of FIG. 10.

Figure 23A:
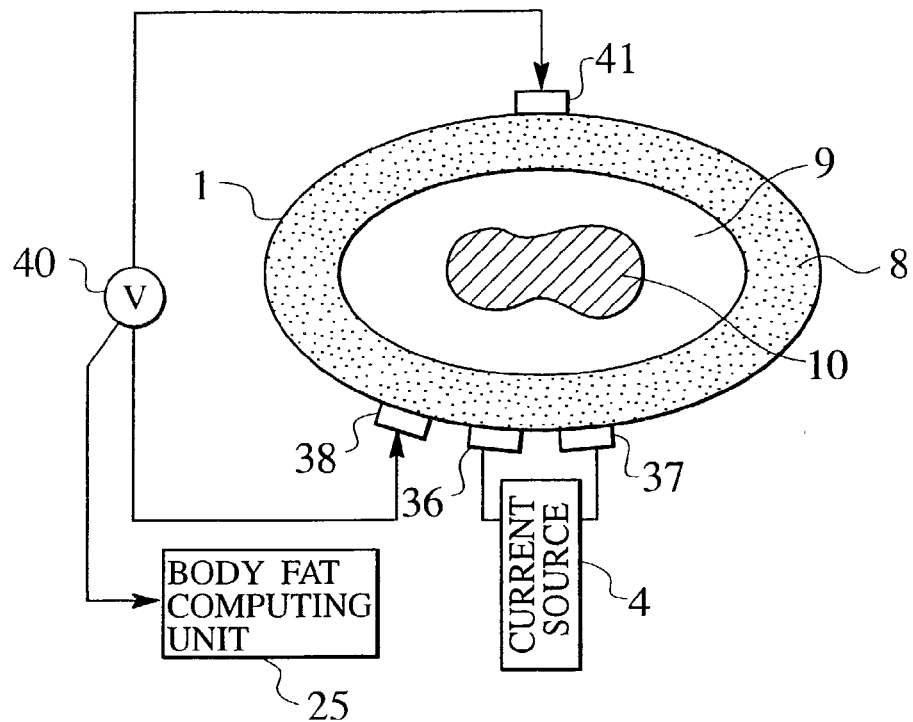
FIGS. 23A and 23B show another example of a body fat measuring apparatus according to the sixth embodiment based on the second aspect.
Figure 23B:
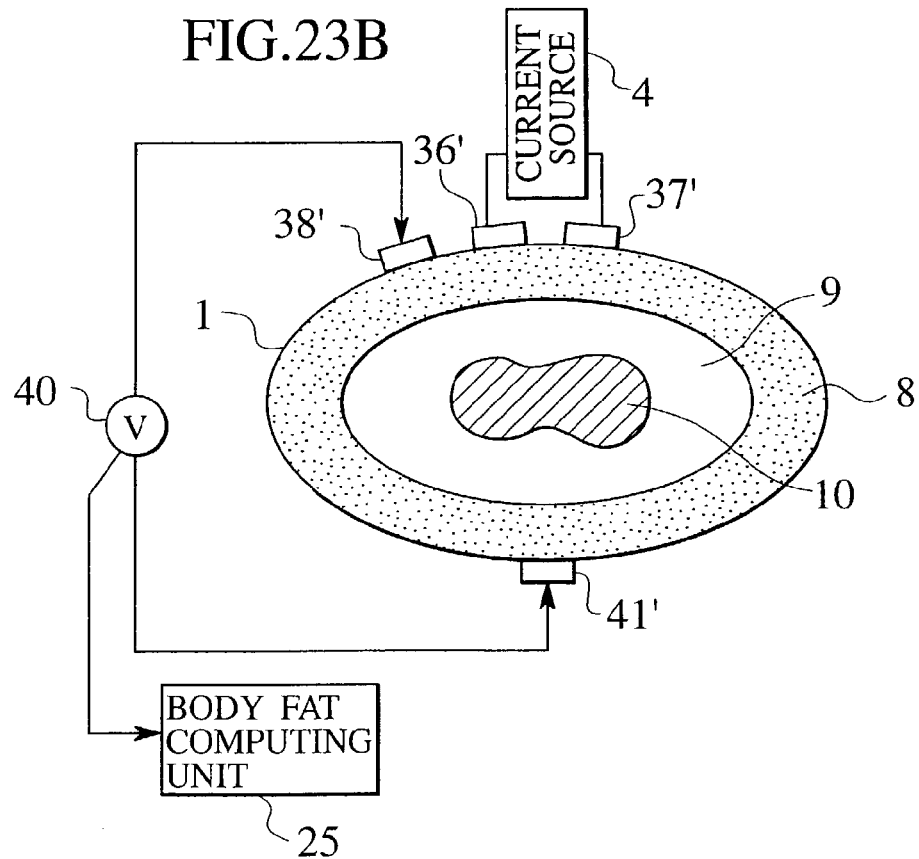

The sixth embodiment will be explained. A body fat measuring apparatus according to the sixth embodiment is made by adding the measuring apparatus of FIG. 22A or FIG. 23A and the measuring apparatus of FIG. 22B or FIG. 23B to the body fat measuring apparatus of the fifth embodiment. It is preferable that the electrodes 36 and 37 of FIG. 22A or 23A are arranged at or adjacent to the electrode 3 of FIG. 24. The electrode 36 or 37 may be equal to the electrode 3. It is preferable that the electrodes 36' and 37' of FIG. 22B or 23B are arranged at or adjacent to the electrode 2 of FIG. 24. The electrode 36' or 37' may be equal to the electrode 2.

A body fat measuring method will be explained. In FIG. 22A or 23A, the voltmeter 40 measures a third voltage generated between the measuring electrodes 38 and 39, or 38 and 41. In FIG. 22B or 23B, the voltmeter 40 measures a fourth voltage generated between the measuring electrodes 38' and 39', or 38' and 41'. The body fat computing unit 25 uses first and second voltages measured with the voltmeter 7 and the third and fourth voltages measured with the voltmeter 40, to compute the quantity of subcutaneous fat 8 like the fifth embodiment.

The third voltage is mainly caused by a voltage drop due to subcutaneous fat 8 around the electrodes 36 and 37, i.e., the electrode 3. The fourth voltage is mainly caused by a voltage drop due to subcutaneous fat 8 around the electrodes 36' and 37', i.e., the electrode 2. The third and fourth voltages are combined with the first and second voltages of the fifth embodiment, to accurately measure the sum of the thicknesses of the subcutaneous fat around the electrodes 3 and 2, or a cross-sectional area of the same. The first to fourth voltages may be measured in any order. Any of the voltages may be measured first.

To compute the sum d+d' of the thickness d of the subcutaneous fat 8 around the current electrode 3 and the thickness d' of the same around the current electrode 2, a correlation expression is prepared in advance to correlate the first to fourth voltages V1, V2, V3, and V4 with the total thickness d+d'. The correlation expression may be approximated by a linear polynomial based on a multivariate analysis. If the quantity d+d' is the absolute value of the thickness of the subcutaneous fat 8, the correlation expression is, for example, $d+d'=a0+a1 \cdot V1 \cdot \epsilon1 \cdot a2 \cdot (V2 \cdot U/L2) \cdot \epsilon2+a3 \cdot V3 \cdot \epsilon3+a4 \cdot V4 \cdot \epsilon4+(a5+a6 \cdot L1/U) \cdot \epsilon1+(a7 \cdot L3/U+a8 \cdot L3'/U+a9 \cdot L3 \cdot L3'/U^2) \cdot \epsilon3+(a10 \cdot L4/U+a11 \cdot L4'/U+a12 \cdot L4 \cdot L4'/U^2) \cdot \epsilon4$, where a0 to a12 are regression coefficients, L1 is the distance between the electrodes 2 and 42, or 3 and 43, L2 is the distance between the electrodes 21 and 22, L3 is the distance between the electrodes 36 and 37, L3' is the distance between the electrodes 36 and 38, L4 is the distance between the electrodes 36' and 37', L4' is the distance between the electrodes 36' and 38', and $\epsilon1$ to $\epsilon4$ are exponential values of characteristic quantities representing the size of the subject 1. For example, they are the first power of a circumferential length U (first power thereof) of the subject 1 and the first power of a longitudinal width W1 or lateral width W2 of the subject 1. The exponent is not limited to 1 and is determined to optimize the correlation. The electrode-to-electrode distances L1, L2, L3, L3', L4, and L4' may be changed in proportion to the circumferential length U of the subject 1. In this case, the correlation expression may be $d+d'=a0+a1 \cdot V1 \cdot \epsilon1-a2 \cdot V2\epsilon2+a3 \cdot V3 \cdot \epsilon3+a4 \cdot V4 \cdot \epsilon4 \cdot a5 \cdot \epsilon1$.

To compute a cross-sectional area S of the subcutaneous fat 8, a correlation expression to correlate the first to fourth voltages V1 to V4 with the cross-sectional area S of the subcutaneous fat is prepared in advance. If the quantity S is the absolute value of the cross-sectional area of the subcutaneous fat 8, the correlation expression is, for example, $S= a0+a1 \cdot V1 \cdot \epsilon1-a2 \cdot (V2 \cdot U/L2) \cdot \epsilon2+a3 \cdot V3 \cdot \epsilon3+a4 \cdot \epsilon4+ (a5+a6 \cdot L1/U) \cdot \epsilon1+(a7 \cdot L3/U+a8 \cdot L3'/U+a9 \cdot L3 \cdot L3'/U^2) \cdot \epsilon3+ (a10 \cdot L4/U+a11 \cdot L4'/U+a12 \cdot L4 \cdot L4'/U^2) \cdot \epsilon4$, where $\epsilon1$ to $\epsilon4$ are typically the square $U^2$ of the circumferential length U of the subject 1, or the product W1·W2 of the longitudinal width W1 and lateral width W2 of the subject 1. The electrode-to-electrode distances L1, L2, L3, L3', L4, and L4' may be changed in proportion to the circumferential length U of the subject 1. In this case, the correlation expression is $S=a0+a1 \cdot V1 \cdot \epsilon1-a2 \cdot V2 \cdot \epsilon2+a3 \cdot V3 \cdot \epsilon3+a4 \cdot V4 \cdot \epsilon4+a5 \cdot \epsilon1$.

A body fat measuring apparatus according to the seventh embodiment consists of the body fat measuring apparatus of FIG. 27 and the measuring apparatus of FIG. 28. The body fat computing unit 25 uses a first voltage measured with the voltmeter 7 of FIG. 27 and a second voltage measured with the voltmeter 7 of FIG. 28, to compute the quantity of subcutaneous fat 8 of a subject 1. The electrode 2 may be equal to the electrode 46, and the electrode 3 may be equal to the electrode 47.

A body fat measuring method will be explained. In the measuring apparatus of FIG. 27, the current source 4 passes a current between the first and second current electrodes 3 and 2, and the voltmeter 7 measures a first voltage generated between the first measuring electrode 44 and the second measuring electrode 45. In the measuring apparatus of FIG. 28, the current source 4 passes a current between the third and fourth current electrodes 47 and 46, and the voltmeter 7 measures a second voltage generated between the third and fourth measuring electrodes 21 and 22. The body fat computing unit 25 uses the first and second voltages measured with the voltmeters 7 to compute the quantity of the subcutaneous fat 8 of the subject 1. The quantity of the subcutaneous fat 8 may be the thickness d of the subcutaneous fat around the electrode 3, or a cross-sectional area S on or around a cross section around which the electrodes are arranged. The first voltage is substantially the sum of a voltage drop caused by the subcutaneous fat 8 around the electrode 3 and a voltage drop caused by the visceral fat 10. The second voltage mainly corresponds to a voltage drop caused by the visceral fat 10. Therefore, subtracting the second voltage from the first voltage precisely provides the thickness of the subcutaneous fat 8 around the electrode 3. The difference between the first and second voltages approximately provides a cross-sectional area of the subcutaneous fat 8. The first and second voltages may be measured in optional order. The second voltage may be measured first and then the first voltage.

To calculate the thickness d of the subcutaneous fat 8 around the current electrode 3 and the cross-sectional area S of the subcutaneous fat 8, a correlation expression is prepared in advance to correlate the first and second voltages V1 and V2 with the fat quantity.

The correlation expression may be made by replacing d+d' of the correlation expression of the fifth embodiment with d and by redefining L1 as the distance between the electrodes 3 and 44. According to the correlation expression and voltages V1 and V2 measured on a given sample, the thickness d or cross-sectional area S of subcutaneous fat of the sample is calculable.

The eighth embodiment will be explained. A body fat measuring apparatus of the eighth embodiment is made by adding the measuring apparatus of FIG. 22A or 23A to the body fat measuring apparatus of the seventh embodiment. It is preferable that the electrodes 36 and 37 of FIGS. 22A and 23A are arranged at or close to the position of the electrode 3 of FIG. 27. The electrode 36 or 37 may be equal to the electrode 3.

A body fat measuring method will be explained. In FIG. 22A or 23A, the voltmeter 40 measures a third voltage generated between the measuring electrodes 38 and 39, or 38 and 41. The body fat computing unit 25 uses first and second voltages measured with the voltmeter 7 and the third voltage measured with the voltmeter 40, to compute the quantity of subcutaneous fat 8 of a subject 1 like the seventh embodiment.

The third voltage is mainly caused by a voltage drop due to the subcutaneous fat 8 around the electrodes 36 and 37, i.e., the electrode 3. Combining the third voltage with the first and second voltages of the seventh embodiment further accurately measures the thickness of the subcutaneous fat 8 around the electrode 3. Measuring order of the first to third voltages is optional. Any one of the voltages may be measured first.

To compute the thickness d of the subcutaneous fat 8 around the current electrode 3 or the cross-sectional area S of the subcutaneous fat 8, a correlation expression is prepared in advance to correlate the first to third voltages V1 to V3 with the fat quantity.

The correlation expression is made, for example, from the correlation expression of the sixth embodiment by setting $\epsilon4=0$, replacing d+d' with d, and redefining L1 as the distance between the electrodes 3 and 44.

The ninth embodiment will be explained. A body fat measuring apparatus according to the ninth embodiment has the same structure as the apparatus of FIG. 8. Like the fourth embodiment of the first aspect, currents are successively supplied in a plurality of directions, and the thickness of subcutaneous fat 8 of a subject 1 is automatically measured at different points along a circumference of the subject 1.

The electrodes 26a to 26h are selected and arranged like the current electrodes and measuring electrodes of FIGS. 27 and 28, to measure first and second voltages. A correlation expression similar to that of the seventh embodiment is prepared, to precisely measure the thicknesses of the subcutaneous fat 8 at different points along the circumference of the subject 1. The electrodes 26a to 26h may be selected and arranged like the current electrodes and measuring electrodes of FIGS. 27, 28, and 22A (or 23A), to measure first to third voltages. A correlation expression similar to that of the eighth embodiment is prepared to further precisely measure the thicknesses of the subcutaneous fat 8 at different points along a circumference of the subject 1. The thicknesses of the subcutaneous fat 8 measured at a plurality of points along a circumference of the subject 1 may be combined with data related to the contour shape of the subject 1 separately measured, so that the computer 35 may roughly provide a tomographic image of the subcutaneous fat 8.

The computer 35 may find a cross-sectional area S of the subcutaneous fat 8 of the subject 1. In this case, a correlation expression to correlate voltages with the cross-sectional area of the subcutaneous fat 8 must be prepared. First voltages $V1^{(1)}, V2^{(1)}, \ldots, Vn^{(1)}$ are measured at n points along a given cross section, and second voltages $V1^{(2)}, V2^{(2)}, \ldots, Vm^{(2)}$ are measured at m points along the same cross section. A correlation expression to correlate these voltages with the cross-sectional area S of the subcutaneous fat 8 is prepared like the seventh embodiment.

The tenth embodiment will be explained. A body fat measuring apparatus according to the tenth embodiment is made of the measuring apparatus of FIG. 24, the measuring apparatus of FIG. 22A or 23A, and the measuring apparatus of FIG. 22B or 23B. The voltmeter 7 of FIG. 24 measures a first voltage generated between the measuring electrodes 42 and 43. The voltmeter 40 of FIG. 22A (or 23A) measures a second voltage generated between the measuring electrodes 38 and 39 (or 38 and 41). The voltmeter 40 of FIG. 22B (or 23B) measures a third voltage generated between the measuring electrodes 38' and 39' (or 38' and 41'). The body fat computing unit 25 uses the measured first to third voltages to compute the quantity of visceral fat 10 of a subject 1. It is preferable that the electrodes 36 and 37 are arranged at or close to the position of the electrode 3. The electrode 36 or 37 may be equal to the electrode 3. It is preferable that the electrodes 36' and 37' are arranged at or close to the position of the electrode 2. The electrode 36' or 37' may be equal to the electrode 2. Instead of the measuring apparatus of FIG. 24, the measuring apparatus of FIG. 25 or FIG. 26 may be employed.

A body fat measuring method will be explained. The voltmeter 7 of FIG. 24 measures a first voltage. The voltmeter 40 of FIG. 22A (or 23A) measures a second voltage. The voltmeter 40 of FIG. 22B (or 23B) measures a third voltage. The body fat computing unit 25 uses the first to third voltages measured with the voltmeters 7 and 40 to compute the quantity of the visceral fat 10. The first voltage is substantially the sum of a voltage drop due to the subcutaneous fat 8 around the electrode 3, a voltage drop due to the visceral fat 10, and a voltage drop due to the subcutaneous fat 8 around the electrode 2. The second voltage substantially corresponds to a voltage drop due to the subcutaneous fat 8 around the electrode 3, and the third voltage substantially corresponds to a voltage drop due to the subcutaneous fat 8 around the electrode 2. As a result, subtracting the second and third voltages from the first voltage provides the quantity of the visceral fat 10. The first to third voltages may be measured in any order. Any one of the voltages may be measured first.

To compute the quantity m of the visceral fat 10, a correlation expression is prepared in advance to correlate the first to third voltages V1 to V3 with the quantity m of the visceral fat. If the quantity m is a relative value such as the ratio of a cross-sectional area of the visceral fat 10 to a total cross-sectional area of the subject 1, or the ratio of the same to a cross-sectional area of a nonfat part 9 around the visceral fat, the simplest form of the correlation expression is, for example, $m = a0 + a1 \cdot V1 - a2 \cdot V2 - a3 \cdot V3$, where a0 to a3 are regression coefficients. If it is known beforehand that the thickness of the subcutaneous fat 8 around the electrode 2 is substantially equal to the thickness of the subcutaneous fat 8 around the electrode 3, the measurement of any one of the second and third voltages can be omitted. In this case, the correlation expression is, for example, $m = a0 + a1 \cdot V1 - a2 \cdot V2$.

If the quantity m is an absolute cross-sectional area of the visceral fat 10, the correlation expression is, for example, $m = a0 + a1 \cdot V1 \cdot \epsilon 1 - a2 \cdot V2 \cdot \epsilon 2 - a3 \cdot V3 \cdot \epsilon 3 + (a4 + a5 \cdot L1/U) \cdot \epsilon 1 + (a6 \cdot L2/U + a7 \cdot L2'/U + a8 \cdot L2 \cdot L2'/U^2) \cdot \epsilon 2 + (a9 \cdot L3/U + a10 \cdot L3'/U + a11 \cdot L3 \cdot L3'/U^2) \cdot \epsilon 3$, where a0 to a11 are regression coefficients, L1 is the distance between the electrodes 2 and 42, or 3 and 43, L2 is the distance between the electrodes 36 and 37, L2' is the distance between the electrodes 36 and 38, L3 is the distance between the electrodes 36' and 37', L3' is the distance between the electrodes 36' and 38', and $\epsilon 1$ to $\epsilon 3$ are the square $U^2$ of a circumferential length U of the subject 1 or the product W1·W2 of a longitudinal width W1 and lateral width W2 of the subject 1. The exponents are not limited to 1 and 2 and are determined to optimize the correlation. The electrode-to-electrode distances L1, L2, L2', L3, and L3' may be changed in proportion to the circumferential length U of the subject 1. In this case, the correlation expression is $m = a0 + a1 \cdot V1 \cdot \epsilon 1 - a2 \cdot V2 \cdot \epsilon 2 - a3 \cdot V3 \cdot \epsilon 3 + a4 \cdot \epsilon 1$.

The apparatus of this embodiment may additionally be provided with an apparatus that is substantially equal to that of FIG. 22 or 23 with the electrodes being arranged at other positions along a circumference of the subject 1. In this case, the voltmeter 40 of the added measuring apparatus measures voltages, which are included in the correlation expression to further precisely compute the quantity m of the visceral fat.

The eleventh embodiment will be explained. A body fat measuring apparatus according to the eleventh embodiment is made by adding the measuring apparatus of FIG. 28 to the measuring apparatus of the tenth embodiment. The voltmeter 7 of FIG. 28 measures a fourth voltage generated between the measuring electrodes 21 and 22. The body fat computing unit 25 uses measured first to fourth voltages, to compute the quantity of visceral fat 10 of a subject 1. The electrode 2 may be equal to the electrode 46, and the electrode 3 may be equal to the electrode 47. The fourth voltage is mainly generated by a voltage drop due to the visceral fat 10, and therefore, combining the fourth voltage with the first to third voltages of the tenth embodiment more precisely measures the quantity of the visceral fat 10. The first to fourth voltages may be measured in optional order. Any one of the voltages may be measured first, to provide the same effect.

To compute the quantity m of the visceral fat 10, a correlation expression is prepared in advance to correlate the first to fourth voltages V1 to V4 with the quantity m of visceral fat. If the quantity m is a relative value such as the ratio of a cross-sectional area of the visceral fat 10 to a total cross-sectional area of the subject 1, or the ratio of the same to a cross-sectional area of a nonfat part 9 around the visceral fat, the simplest form of the correlation expression is, for example, $m = a0 + a1 \cdot V1 - a2 \cdot V2 - a3 \cdot V3 + a4 \cdot V4$, where a0 to a4 are regression coefficients. If it is known beforehand that the thickness of the subcutaneous fat 8 around the electrode 2 is substantially equal to the thickness of the subcutaneous fat 8 around the electrode 3, the measurement of any one of the second and third voltages may be omitted. In this case, the correlation expression is, for example, m=a0+a1·V1−a2·V2+a4·V4.

If the quantity m is an absolute cross-sectional area of the visceral fat 10, the correlation expression is, for example, the same as that for S of the sixth embodiment.

The twelfth embodiment will be explained. A body fat measuring apparatus according to the twelfth embodiment consists of the measuring apparatus of FIG. 27 and the measuring apparatus of FIG. 22A or 23A. The voltmeter 7 of FIG. 27 measures a first voltage generated between the measuring electrodes 44 and 45. The voltmeter 40 of FIG. 22A (or 23A) measures a second voltage generated between the measuring electrodes 38 and 39 (or 38 and 41). The body fat computing unit 25 uses the measured first and second voltages to compute the quantity of visceral fat 10 of a subject 1. It is preferable that the electrodes 36 and 37 are arranged at or close to the position of the electrode 3. The electrode 36 or 37 may be equal to the electrode 3.

A body fat measuring method will be explained. The voltmeter 7 of FIG. 27 measures a first voltage, and the voltmeter 40 of FIG. 22A (or 23A) measures a second voltage. Based on the measured first and second voltages, the body fat computing unit 25 computes the quantity of the visceral fat 10. The first voltage is substantially the sum of a voltage drop caused by the subcutaneous fat 8 around the electrode 3 and a voltage drop caused by the visceral fat 10. The second voltage is substantially caused by a voltage drop due to the subcutaneous fat 8 around the electrode 3. Accordingly, subtracting the second voltage from the first voltage provides the quantity of the visceral fat 10. The first and second voltages are measurable in optional order. Any one of the voltages may be measured first.

To compute the quantity m of the visceral fat 10, a correlation expression is prepared in advance to correlate the first and second voltages V1 and V2 with the quantity m of visceral fat. If the quantity m is a relative value such as the ratio of a cross-sectional area of the visceral fat 10 to a total cross-sectional area of the subject 1, or the ratio of the same to a cross-sectional area of a nonfat part 9 around the visceral fat, the simplest form of the correlation expression is, for example, m=a0+a1·V1−a2·V2, where a0 to a2 are regression coefficients. If the quantity m is an absolute cross-sectional area of the visceral fat 10, the correlation expression is, for example, that of the tenth embodiment in which $\epsilon 3=0$ and L1 is redefined as the distance between the electrodes 3 and 44.

The measuring apparatus of this embodiment may be provided with an apparatus that is substantially the same as that of FIG. 22 or 23 with the electrodes being arranged at different positions along a circumference of the subject 1. The voltmeter 40 of the added measuring apparatus measures voltages, which are included in the correlation expression, to further precisely calculate the quantity m of the visceral fat 10.

The thirteenth embodiment will be explained. A body fat measuring apparatus according to the thirteenth embodiment is made by adding the measuring apparatus of FIG. 28 to the measuring apparatus of the twelfth embodiment. The voltmeter 7 of FIG. 28 measures a third voltage generated between the measuring electrodes 21 and 22. Based on measured first to third voltages, the body fat computing unit 25 computes the quantity of visceral fat 10 of a subject 1. The electrode 2 may be equal to the electrode 46, and the electrode 3 may be equal to the electrode 47. The third voltage is mainly caused by a voltage drop due to the visceral fat 10. Accordingly, combining the third voltage with the first and second voltages of the twelfth embodiment further improves the measuring accuracy of the quantity of the visceral fat 10. The first to third voltages may be measured in optional order. Any one of the voltages may be measured first.

To compute the quantity m of the visceral fat 10, a correlation expression is prepared in advance to correlate the first to third voltages V1 to V3 with the quantity m of visceral fat. If the quantity m is a relative value such as the ratio of a cross-sectional area of the visceral fat 10 to a total cross-sectional area of the subject 1, or the ratio of the same to a cross-sectional area of a nonfat part 9 around the visceral fat, the simplest form of the correlation expression will be, for example, m=a0+a1·V1−a2·V2+a3·V3, where a0 to a3 are regression coefficients. If the quantity m is an absolute cross-sectional area of the visceral fat 10, the correlation expression is, for example, that of the sixth embodiment in which $\epsilon 4=0$, S is replaced with m, and L1 is redefined as the distance between the electrodes 3 and 44.

A fourteenth embodiment will be explained. A body fat measuring apparatus according to the fourteenth embodiment is constituted like that of FIG. 8, successively supplies currents in a plurality of directions, and automatically measures a visceral fat quantity in a subject 1. The data input unit 33 enters a correlation expression to correlate voltages with a visceral fat quantity m into the computer 35 beforehand. The computer 35 employs the correlation expression to find a visceral fat quantity m, which is transferred to the data output unit 34. The data output unit 34 displays the quantity m. The other parts and measurement method of this embodiment are the same as those of the fourth embodiment of the first aspect.

The electrodes 26a to 26h are successively selected and arranged like the current electrodes and measuring electrodes of FIGS. 27 and 22A (or 23A), to measure n first voltages $V1^{(1)}, V2^{(1)}, \ldots, Vn^{(1)}$ and n second voltages $V1^{(2)}, V2^{(2)}, \ldots, Vn^{(2)}$. Like the twelfth embodiment, a correlation expression of $m=a0+a1^{(1)} \cdot V1^{(1)}+a2^{(1)} \cdot V2^{(1)}+ \ldots +an^{(1)} \cdot Vn^{(1)} - a1^{(2)} \cdot V1^{(2)} - a2^{(2)} \cdot V2^{(2)} - \ldots - an^{(2)} \cdot Vn^{(2)}$ is prepared to precisely measure the quantity of the visceral fat 10 of the subject 1. It is also possible to successively select and arrange the electrodes 26a to 26h like the current electrodes and measuring electrodes of FIGS. 27, 22A (or 23A), and 28 to measure n first voltages $V1^{(1)}, V2^{(1)}, \ldots, Vn^{(1)}$, n second voltages $V1^{(2)}, V2^{(2)}, \ldots, Vn^{(2)}$, and m third voltages $V1^{(3)}, V2^{(3)}, \ldots, Vm^{(3)}$. Like the thirteenth embodiment, a correlation expression of $m=a0+a1^{(1)} \cdot V1^{(1)}+a2^{(1)} \cdot V2^{(1)}, \ldots, +an^{(3)} \cdot Vn^{(1)} - a1^{(2)} \cdot V1^{(2)} - a2^{(2)} \cdot V2^{(2)} - \ldots -an^{(2)} \cdot Vn^{(2)} + a1^{(3)} \cdot V1^{(3)} + a2^{(3)} \cdot V2^{(3)} + \ldots + am^{(3)} \cdot Vm^{(3)}$ is prepared to precisely measure the quantity of the visceral fat 10.

Similarly, the electrodes 26a to 26h may successively be selected and arranged like the current electrodes and measuring electrodes of FIGS. 24, 22A (or 23A), and 22B (or 23B), to measure a plurality of first to third voltages. Based on the measured voltages, a correlation expression like that of the tenth embodiment precisely computes the quantity of the visceral fat 10. Also, the electrodes 26a to 26h may successively be selected and arranged like the current electrodes and measuring electrodes of FIGS. 24, 28, 22A (or 23A), and 22B (or 23B), to measure a plurality of first to fourth voltages. Based on the measured voltages, a correlation expression like that of the eleventh embodiment precisely computes the quantity of the visceral fat 10.

According to the first to fourteenth embodiments, measurements may be carried out at a plurality of current frequencies, and the measurements may be compared with one another to improve the reliability of the measurements.

The body fat measuring apparatuses of the first to third aspects may reduce contact resistance between the electrodes and a subject, by applying conductive gel or conductive gel sheets between the electrodes and the subject. The electric impedance of a human subject changes within a day. Accordingly, a measured voltage may be corrected according to the time of the measurement, to correct an error in a calculated body fat quantity due to an hourly variation in the electric impedance of the subject. The stomach of a human body changes its state before and after a meal. Accordingly, a measured voltage may be corrected according to an elapsed time after a meal to the measurement. This corrects an error in a computed body fat quantity caused by the meal.

The body fat measuring apparatuses of the first to third aspects of the present invention may be combined to form another apparatus. For example, the body fat measuring apparatus of the first embodiment of the third aspect measures the sum of subcutaneous and visceral fat quantities. From the sum, a visceral fat quantity measured with the body fat measuring apparatus of the fourth embodiment of the second aspect is subtracted to provide a highly accurate subcutaneous fat quantity. This results in providing the ratio (V/S) of the visceral fat quantity to the subcutaneous fat quantity. Alternatively, the body fat measuring apparatus of the first embodiment of the third aspect measures the sum of subcutaneous and visceral fat quantities, and from the sum, a subcutaneous fat quantity (a cross-sectional area of subcutaneous fat) measured with the body fat measuring apparatus of the fourth embodiment of the first aspect is subtracted, to provide a visceral fat quantity.

There is a medical view that visceral fat causes lifestyle-related illnesses such as hyperlipemia, diabetes, hypertension, etc. Accordingly, health advice may be displayed on the data output unit of the apparatus on the basis of a visceral fat quantity measured with the body fat measuring apparatus of the present invention. Based on a subcutaneous fat quantity measured with the body fat measuring apparatus of the present invention, cosmetic advice may be displayed on the data output unit. The sum of subcutaneous and visceral fat quantities measured with the body fat measuring apparatus of the present invention may be correlated with a body fat ratio handled by conventional body fat meters, so that the data output unit may display the body fat ratio.

The present invention is applicable to estimate not only a visceral fat quantity but also a liver fat quantity. The apparatus of the present invention is applicable not only to the body of a subject but also to the thigh or the upper arm of the subject, to measure a subcutaneous fat quantity of the part. Objects to which the present invention is applicable are not only human bodies but also livestock such as hogs and cows and fish such as tuna.

The present invention is capable of measuring a subcutaneous fat quantity and an internal fat quantity of a given object.

UTILIZATION IN INDUSTRY

As explained above, the method of and apparatus for measuring body fat according to the present invention are capable of measuring a body fat quantity more easily and precisely than the impedance CT method. In particular, the method and apparatus of the present invention are capable of easily and precisely measuring the thickness, cross-sectional area, or volume of a subcutaneous fat of a subject almost without the influence of the quantity and distribution of visceral fat in the subject. The method and apparatus of the present invention can eliminate the remaining influence of the quantities and distributions of other media including the visceral fat in the subject and further precisely measure the thickness, cross-sectional area, or volume of the subcutaneous fat of the subject. The method and apparatus of the present invention are also capable of easily and precisely measuring a visceral fat quantity of the subject almost without the influence of the quantity and distribution of the subcutaneous fat of the subject. The present invention is capable of eliminating the remaining influence of the quantity and distribution of the subcutaneous fat of the subject and further precisely measuring the visceral fat quantity of the subject. The body fat measuring apparatus according to the present invention is particularly effective as a body fat meter.

What is claimed is:

1. A body fat measuring method comprising:
   a step of passing a current between two current electrodes arranged on a circumference of a subject, a distance between the electrodes being sufficiently shorter than a circumferential length of the subject;
   a step of measuring a first voltage generated between a first measuring electrode arranged adjacent to one of the two current electrodes and a second measuring electrode arranged substantially opposite to the two current electrodes across the subject; and
   a step of computing a subcutaneous fat thickness of the subject according to the first voltage.

2. The body fat measuring method of claim 1, wherein the step of computing includes:
   a step of measuring a second voltage generated when a current is passed in a direction substantially crossing the subject; and
   a step of correcting the first voltage according to the second voltage and computing a subcutaneous fat thickness of the subject according to the corrected first voltage.

3. A body fat measuring method comprising:
   a step of passing a current between two current electrodes arranged on a circumference of a subject, a distance between the electrodes being sufficiently shorter than a circumferential length of the subject;
   a step of measuring a first voltage generated between two measuring electrodes that are each arranged adjacent to the two current electrodes;
   a step of measuring a second voltage generated when a current is passed in a direction substantially crossing the subject; and
   a step of correcting the first voltage according to the second voltage and computing a subcutaneous fat quantity of the subject according to the corrected first voltage.

4. A body fat measuring method comprising:
   a step of passing a current between two current electrodes arranged on a circumference of a subject substantially opposite to each other across the subject;
   a step of measuring a spatial potential gradient occurring on the circumference of the subject substantially at an intermediate position between the two current electrodes; and
   a step of computing a fat quantity of the subject according to the spatial potential gradient.

5. The body fat measuring method of claim 4, including:
   a step of measuring a first voltage generated between two measuring electrodes arranged substantially at an intermediate position between the two current electrodes on the circumference of the subject, the distance between the measuring electrodes being sufficiently shorter than a circumferential length of the subject, and finding the spatial potential gradient accordingly.

6. The body fat measuring method of claim 5, wherein the fat quantity is a visceral fat quantity.

7. The body fat measuring method of claim 4, including:
a step of measuring a second voltage generated when a current is passed between two current electrodes arranged on the circumference of the subject, the distance between the two current electrodes being sufficiently shorter than a circumferential length of the subject; and
a step of correcting the spatial potential gradient according to the second voltage and computing a fat quantity of the subject according to the corrected spatial potential gradient.

8. The body fat measuring method of claim 4, wherein the fat quantity is a visceral fat quantity.

9. The body fat measuring method of claim 7, wherein the fat quantity is a visceral fat quantity.

10. A body fat measuring method comprising:
a step of passing a current between two current electrodes arranged on a circumference of a subject substantially opposite to each other across the subject;
a step of measuring a voltage generated between two measuring electrodes that are each arranged adjacent to the two current electrodes; and
a step of computing, according to the voltage, the ratio of a cross-sectional area of body fat of the subject on or near a cross section around which the electrodes are arranged to a cross-sectional area of the subject.

11. The body fat measuring method of claim 10, wherein the cross-sectional area of the body fat is the sum of cross-sectional areas of subcutaneous fat and visceral fat.

12. A body fat measuring method comprising:
a step of passing a current between two current electrodes arranged on a circumference of a subject substantially opposite to each other across the subject;
a step of measuring a voltage generated between a measuring electrode arranged adjacent to one of the two current electrodes and a measuring electrode arranged on the circumference of the subject substantially at an intermediate position between the two current electrodes; and
a step of computing, according to the voltage, the ratio of a cross-sectional area of body fat of the subject on or near a cross section around which the electrodes are arranged to a cross-sectional area of the subject.

13. The body fat measuring method of claim 12, wherein the cross-sectional area of the body fat is the sum of cross-sectional areas of subcutaneous fat and visceral fat.

14. A body fat measuring method comprising:
a step of passing a current between two current electrodes arranged on a circumference of a subject substantially opposite to each other across the subject;
a step of measuring a voltage generated between two measuring electrodes that are each arranged adjacent to the two current electrodes; and
a step of multiplying the voltage by a power of a characteristic quantity representing the size of the subject, and according to the product, computing a fat quantity of the subject.

15. The body fat measuring method according to claim 14, wherein the fat quantity is the sum of subcutaneous and visceral fat quantities.

16. The body fat measuring method according to claim 15, wherein the characteristic quantity representing the size of the subject is a width or circumferential length of the subject.

17. The body fat measuring method according to claim 14, wherein the characteristic quantity representing the size of the subject is a width or circumferential length of the subject.

18. A body fat measuring method comprising:
a step of passing a current between two current electrodes arranged on a circumference of a subject substantially opposite to each other across the subject;
a step of measuring a voltage generated between a measuring electrode arranged adjacent to one of the two current electrodes and a measuring electrode arranged on the circumference of the subject substantially at an intermediate position between the two current electrodes; and
a step of multiplying the voltage by a power of a characteristic quantity representing the size of the subject, and according to the product, computing a fat quantity of the subject.

19. The body fat measuring method according to claim 18, wherein the fat quantity is the sum of subcutaneous and visceral fat quantities.

20. The body fat measuring method according to claim 19, wherein the characteristic quantity representing the size of the subject is a width or circumferential length of the subject.

21. The body fat measuring method according to claim 18, wherein the characteristic quantity representing the size of the subject is a width or circumferential length of the subject.

22. A body fat measuring method comprising:
a step of passing a current between first and second current electrodes arranged on a circumference of a subject substantially opposite to each other across the subject, measuring a first voltage generated between first and second measuring electrodes that are arranged adjacent to the first and second current electrodes, respectively, passing a current between third and fourth current electrodes arranged on the circumference of the subject substantially opposite to each other across the subject, and measuring a spatial potential gradient occurring on the circumference of the subject substantially at an intermediate position between the third and fourth current electrodes; and
a step of computing a subcutaneous fat quantity of the subject according to the first voltage and spatial potential gradient.

23. A body fat measuring method comprising:
a step of passing a current between first and second current electrodes arranged on a circumference of a subject substantially opposite to each other across the subject, measuring a first voltage generated between a first measuring electrode arranged adjacent to the first current electrode and a second measuring electrode arranged on the circumference of the subject substantially at an intermediate position between the first and second current electrodes, passing a current between third and fourth current electrodes arranged on the circumference of the subject substantially opposite to each other across the subject, and measuring a spatial potential gradient occurring on the circumference of the subject substantially at an intermediate position between the third and fourth current electrodes; and
a step of computing a subcutaneous fat quantity of the subject according to the first voltage and spatial potential gradient.

24. A body fat measuring method comprising:

a step of passing a current between first and second current electrodes arranged on a circumference of a subject substantially opposite to each other across the subject, measuring a first voltage generated between first and second measuring electrodes that are arranged adjacent to the first and second current electrodes, respectively, and measuring a second voltage generated when a current is passed between third and fourth current electrodes arranged on the circumference of the subject, a distance between the third and fourth current electrodes being; sufficiently shorter than a circumferential length of the subject; and a step of computing a visceral fat quantity of the subject according to the first and second voltages.

25. The body fat measuring method according to claim 24, wherein the third and fourth current electrodes are arranged at or around the position of the first or second current electrode.

26. A body fat measuring method comprising:

a step of passing a current between first and second current electrodes arranged on a circumference of a subject substantially opposite to each other across the subject, measuring a first voltage generated between a first measuring electrode arranged adjacent to the first current electrode and a second measuring electrode arranged on the circumference of the subject substantially at an intermediate position between the first and second current electrodes, and measuring a second voltage generated when a current is passed between third and fourth current electrodes arranged on the circumference of the subject, a distance between the third and fourth current electrodes being sufficiently shorter than a circumferential length of the subject; and a step of computing a visceral fat quantity of the subject according to the first and second voltages.

27. The body fat measuring method according to claim 26, wherein the third and fourth current electrodes are arranged at or around the position of the first or second current electrode.

28. A body fat measuring apparatus comprising:

two current electrodes adapted to be arranged on a circumference of a subject, a distance between the electrodes being sufficiently shorter than a circumferential length of the subject;

a first measuring electrode adapted to be arranged adjacent to one of the two current electrodes and a second measuring electrode adapted to be arranged substantially opposite to the two current electrodes across the subject;

measuring means to pass a current between the two current electrodes and measure a first voltage generated between the first and second measuring electrodes; and body fat computing means to calculate a subcutaneous fat thickness of the subject according to the first voltage measured with the measuring means.

29. A body fat measuring apparatus comprising:

two current electrodes adapted to be arranged on a circumference of a subject, a distance between the electrodes being sufficiently shorter than a circumferential length of the subject;

two measuring electrodes that are each adapted to be arranged adjacent to the two current electrodes;

measuring means to pass a current between the two current electrodes, measure a first voltage generated between the measuring electrodes, and measure a second voltage generated when a current is passed in a direction substantially crossing the subject; and body fat computing means to correct the first voltage according to the second voltage measured with the measuring means and compute a subcutaneous fat quantity of the subject according to the corrected first voltage.

30. A body fat measuring apparatus comprising:

two current electrodes adapted to be arranged on a circumference of a subject substantially opposite to each other across the subject;

measuring means to pass a current between the two current electrodes and measure a spatial potential gradient occurring on the circumference of the subject substantially at an intermediate position between the two current electrodes; and body fat computing means to compute a fat quantity of the subject according to the spatial potential gradient measured with the measuring means.

31. A body fat measuring apparatus comprising:

two current electrodes adapted to be arranged on a circumference of a subject substantially opposite to each other across the subject;

two measuring electrodes that are each adapted to be arranged adjacent to the two current electrodes;

measuring means to pass a current between the two current electrodes and measure a voltage generated between the measuring electrodes; and body fat computing means to compute, according to the voltage measured with the measuring means, the ratio of a cross-sectional area of body fat of the subject on or near a cross section around which the electrodes are arranged to a cross-sectional area of the subject.

32. A body fat measuring apparatus comprising:

two current electrodes adapted to be arranged on a circumference of a subject substantially opposite to each other across the subject;

a measuring electrode adapted to be arranged adjacent to one of the two current electrodes and a measuring electrode arranged on the circumference of the subject substantially at an intermediate position between the two current electrodes;

measuring means to pass a current between the two current electrodes and measure a voltage generated between the measuring electrodes; and body fat computing means to compute, according to the voltage measured with the measuring means, the ratio of a cross-sectional area of body fat of the subject on or near a cross section around which the electrodes are arranged to a cross-sectional area of the subject.

33. A body fat measuring apparatus comprising:

two current electrodes adapted to be arranged on a circumference of a subject substantially opposite to each other across the subject;

two measuring electrodes that are each adapted to be arranged adjacent to the two current electrodes;

measuring means to pass a current between the two current electrodes and measure a voltage generated between the measuring electrodes; and body fat computing means to multiply the voltage measured with the measuring means by a power of a characteristic quantity representing the size of the subject, and according to the product, compute a fat quantity of the subject.

34. A body fat measuring apparatus comprising:

two current electrodes adapted to be arranged on a circumference of a subject substantially opposite to each other across the subject;

a measuring electrode adapted to be arranged adjacent to one of the two current electrodes and a measuring electrode arranged on the circumference of the subject substantially at an intermediate position between the two current electrodes;

measuring means to pass a current between the two current electrodes and measure a voltage generated between the measuring electrodes; and body fat computing means to multiply the voltage measured with the measuring means by a power of a characteristic quantity representing the size of the subject, and according to the product, compute a fat quantity of the subject.

35. A body fat measuring apparatus comprising:

first and second current electrodes adapted to be arranged on a circumference of a subject substantially opposite to each other across the subject;

third and fourth current electrodes adapted to be arranged on the circumference of the subject substantially opposite to each other across the subject;

first and second measuring electrodes adapted to be arranged adjacent to the first and second current electrodes, respectively;

measuring means to pass a current between the first and second current electrodes, measure a first voltage generated between the first and second measuring electrodes, pass a current between the third and fourth current electrodes, and measure a spatial potential gradient occurring substantially at an intermediate position between the third and fourth current electrodes; and body fat computing means to compute a subcutaneous fat quantity of the subject according to the first voltage and spatial potential gradient measured with the measuring means.

36. A body fat measuring apparatus comprising:

first and second current electrodes adapted to be arranged on a circumference of a subject substantially opposite to each other across the subject;

third and fourth current electrodes adapted to be arranged on the circumference of the subject substantially opposite to each other across the subject;

a first measuring electrode adapted to be arranged adjacent to the first current electrode and a second measuring electrode adapted to be arranged on the circumference of the subject substantially at an intermediate position between the first and second current electrodes;

measuring means to pass a current between the first and second current electrodes, measure a first voltage generated between the first and second measuring electrodes, pass a current between the third and fourth current electrodes, and measure a spatial potential gradient occurring substantially at an intermediate position between the third and fourth current electrodes; and body fat computing means to compute a subcutaneous fat quantity of the subject according to the first voltage and spatial potential gradient measured with the measuring means.

37. A body fat measuring apparatus comprising:

first and second current electrodes adapted to be arranged on a circumference of a subject substantially opposite to each other across the subject;

third and fourth current electrodes adapted to be arranged on the circumference of the subject, a distance between the third and fourth current electrodes being sufficiently shorter than a circumferential length of the subject;

first and second measuring electrodes adapted to be arranged adjacent to the first and second current electrodes, respectively;

measuring means to pass a current between the first and second current electrodes, measure a first voltage generated between the first and second measuring electrodes, and measure a second voltage generated when a current is passed between the third and fourth current electrodes; and body fat computing means to compute a visceral fat quantity of the subject according to the first and second voltages measured with the measuring means.

38. A body fat measuring apparatus comprising:

first and second current electrodes adapted to be arranged on a circumference of a subject substantially opposite to each other across the subject;

third and fourth current electrodes adapted to be arranged on the circumference of the subject, a distance between the third and fourth current electrodes being sufficiently shorter than a circumferential length of the subject;

a first measuring electrode adapted to be arranged adjacent to the first current electrode and a second measuring electrode adapted to be arranged on the circumference of the subject substantially at an intermediate position between the first and second current electrodes;

measuring means to pass a current between the first and second current electrodes, measure a first voltage generated between the first and second measuring electrodes, and measure a second voltage generated when a current is passed between the third and fourth current electrodes; and body fat computing means to compute a visceral fat quantity of the subject according to the first and second voltages measured with the measuring means.

39. The body fat measuring method of claim 5, including:

a step of measuring a second voltage generated when a current is passed between two current electrodes arranged on the circumference of the subject, the distance between the two current electrodes being sufficiently shorter than a circumferential length of the subject; and a step of correcting the spatial potential gradient according to the second voltage and computing a fat quantity of the subject according to the corrected spatial potential gradient.

40. The body fat measuring method of claim 39, wherein the fat quantity is a visceral fat quantity.

41. A body fat measuring method comprising:

a step of passing a current between two current electrodes arranged on a circumference of a subject, a distance between the electrodes being sufficiently shorter than a circumferential length of the subject;

a step of measuring a first voltage generated between a first measuring electrode arranged adjacent to one of the two current electrodes and a second measuring electrode arranged substantially opposite to the two current electrodes across the subject;

a step of measuring a second voltage generated when a current is passed in a direction substantially crossing the subject; and a step of correcting the first voltage according to the second voltage and computing a subcutaneous fat quantity of the subject according to the corrected first voltage.

* * * * *